(12) United States Patent
Jiang et al.

(10) Patent No.: US 9,089,586 B2
(45) Date of Patent: *Jul. 28, 2015

(54) LEVOCARRIMYCIN, PHARMACEUTICAL COMPOSITIONS, PREPARATION METHODS AND USES THEREOF

(75) Inventors: Yang Jiang, Liaoning (CN); Yuyou Hao, Liaoning (CN)

(73) Assignee: SHENYANG TONGLIAN GROUP CO., LTD., Shenyang (CN)

( * ) Notice: Subject to any disclaimer, the term of this patent is extended or adjusted under 35 U.S.C. 154(b) by 188 days.

This patent is subject to a terminal disclaimer.

(21) Appl. No.: 13/699,358

(22) PCT Filed: May 25, 2011

(86) PCT No.: PCT/CN2011/074658
§ 371 (c)(1),
(2), (4) Date: Feb. 6, 2013

(87) PCT Pub. No.: WO2011/147316
PCT Pub. Date: Dec. 1, 2011

(65) Prior Publication Data
US 2013/0150316 A1 Jun. 13, 2013

(30) Foreign Application Priority Data
May 25, 2010 (CN) ............................ 201010182027

(51) Int. Cl.
| | |
|---|---|
| *A61K 31/7048* | (2006.01) |
| *A61P 31/00* | (2006.01) |
| *A61P 31/04* | (2006.01) |
| *C12P 19/62* | (2006.01) |
| *C07H 17/08* | (2006.01) |

(52) U.S. Cl.
CPC ............ *A61K 31/7048* (2013.01); *C07H 17/08* (2013.01); *C12P 19/62* (2013.01)

(58) Field of Classification Search
CPC ........... A61K 31/7048; A61K 2300/00; C07H 17/08; C12P 19/62
USPC ............................................... 514/30; 435/76
See application file for complete search history.

(56) References Cited

U.S. PATENT DOCUMENTS 8,778,896 B2 * 7/2014 Jiang et al. ...................... 514/30

FOREIGN PATENT DOCUMENTS

| CN | 1405299 | | 3/2003 | |
|---|---|---|---|---|
| CN | 1554355 | * | 12/2004 | ......... A61K 31/7048 |
| CN | 1554355 A | * | 12/2004 | ......... A61K 31/7048 |

OTHER PUBLICATIONS

International Search Report issued on Sep. 8, 2011, by the Chinese Patent Office as the International Searching Authority for the International Appl. No. PCT/CN2011/074658.

* cited by examiner

*Primary Examiner* — Ganapathy Krishnan
(74) *Attorney, Agent, or Firm* — Buchanan Ingersoll & Rooney PC

(57) ABSTRACT

The present invention relates to levocarrimycin, its pharmaceutical compositions, preparation methods and application. Levocarrimycin is a mixture of isovalerylspiramycin III, II and I as main components and contains some isobutyrylspiramycin III and II, butyrylspiramycin III and II, propionylspiramycin III and II, as well as acetylspiramycin III and II, among which, the content of isovalerylspiramycin III is no less than 30 wt %, the total content of isovalerylspiramycin III, II and I is no less than 60 wt %, and the content of acylspiramycin is 80-98 wt %. Specific optical rotation of said levocarrimycin is $[\alpha]_D = -52° \sim -57°$ in the solution of 0.02 g/ml chloroform at temperature of 25° C. The present invention also relates to the crystalline compound of isovalerylspiramycin III, II or I in levocarrimycin, and pharmaceutical compositions containing the said levocarrimycin. In present invention, the active components in levocarrimycin or its pharmaceutical compositions have optical activity and excellent anti-infective effect.

24 Claims, 5 Drawing Sheets

LEVOCARRIMYCIN, PHARMACEUTICAL COMPOSITIONS, PREPARATION METHODS AND USES THEREOF

FIELD OF THE INVENTION

The present invention relates to the field of carrimycin raw medicine and pharmaceutical preparations thereof, specifically to a macrolide genetically-engineered antibiotic, in particular to levocarrimycin, its preparation methods and uses in preparing drugs for treating and preventing infectious diseases.

BACKGROUND OF THE INVENTION

Carrimycin is a new derivative of spiramycin developed by adopting genetic engineering technology, which is originally named biotechspiramycin and formerly named biotechmycin [Patent No.: ZL97104440.6]. According to the "Rules for Chinese Approved Drug Names", and upon technical review and confirmation of Chinese Pharmacopoeia Commission, the Chinese generic name of biotechspiramycin is changed to carrimycin.

Carrimycin is a fermentation product of genetically-engineered bacteria. The chemical structure of carrimycin mainly comprises 4"-isovalerylspiramycin, including 4"-isovalerylspiramycin I, II, III, and about 6 kinds of 4"-hydroxy acylated spiramycin, so the chemical name is 4"-acylspiramycin. Chemical structural form a of main component of carrimycin is as shown in form a (1):

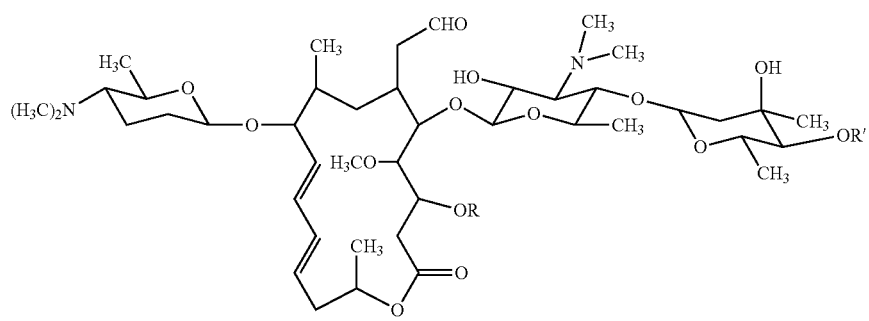

(1)

in which:

|                        | R           | R'              |
|------------------------|-------------|-----------------|
| Isovalerylspiramycin I | H           | $COCH_2CH(CH_3)_2$ |
| Isovalerylspiramycin II | $COCH_3$   | $COCH_2CH(CH_3)_2$ |
| Isovalerylspiramycin III | $COCH_2CH_3$ | $COCH_2CH(CH_3)_2$ |

Carrimycin is a 16-membered ring macrolide antibiotic, which inhibits the protein synthesis by combining with ribosome of bacterium.

In vitro test results show that carrimycin is effective against gram-positive bacteria, especially some drug-resistance bacteria such as β-lactam resistance *staphylococcus aureus* and erythrocin-resistance *staphylococcus aureus*, and has no significant cross drug resistance with similar drugs. Meanwhile, carrimycin has antibacterial activity for mycoplasma and chlamydia, as well as some gram-negative bacteria, good antibacterial activity and tissue permeability for epidemic toxoplasm and *legionella*, and still has potential immuno-regulation function. The antibacterial activity in vivo is much better than that in vitro (ZL200310122420.9). Clinical research shows that by taking carrimycin tablets 0.2-0.4 mg everyday for 5~7 days, it is suitable for treating acute bacterial pharyngitis and acute suppurative tonsillitis caused by pyogenic *streptococcus*; bacterial nasosinusitis and acute bronchitis caused by sensitized bacteria; mild pneumonia caused by *streptococcus pneumonia, haemophilus influenza* and *mycoplasma* pneumonia; nongonoccal urethritis caused by mycoplasma and chlamydia; infectious diseases such as skin and soft tissue infection, periodontitis and otitis media caused by sensitized bacteria. The total effective rate is 92.68%. Carrimycin is safe and effective.

Pharmacokinetics study shows that active components of carrimycin are mainly isovalerylspiramycin I, II and III. Carrimycin quickly metabolizes to spiramycin in vivo. According to $AUC_{0-t}$ of parent drug isovalerylspiramycin I, II and II and active metabolite spiramycin I, II and III, the absolute bioavailability by oral administration is 91.6% averagely. It is reported that the absolute bioavailability of spiramycin by oral administration is 30~40% (Frydman A M et al J Antimicrob Chemother. 1988, 22 (suppl B):93-103). It shows that the isovalerylspiramycin significantly improves the bioavailability of active component spiramycin. Single dose carrimycin is eliminated slowly. T1/2 is between 23~27 hours.

Researches on the active components of carrimycin show that a plurality of chiral carbon atoms exists in the molecular structure of active components of carrimycin: isovalerylspiramycin I, II and III. Chirality is a basic attribute of three-dimensional body and one of the essential attributes of nature. Biological macromolecules including protein, polysaccharide, nucleic acid and enzyme as important basis of vital movement often have important physiological functions. Chiral drug is a pair of enantiomers of material object and mirror image obtained after molecular structure of drug is introduced into the chiral center. These enantiomers are basically the same regarding physicochemical properties but different in optical rotation. The enantiomers are respectively named R-type (dextrorotatory) or S-type (sinistral), and racemic. In recent 20 years, as pharmaceutical research is more intensive, it has been proved that the difference of drug enantiomer's affinity with receptor caused by the difference of drug enantiomer's stereoselectivity leads to great difference in pharmacological action. Enantiomer with high activity among chiral drugs is called eutomer; while the one with low or no activity is called distomer. In many cases, the distomer not only has no pharmacological action, but also offset that of eutomer. Sometimes, severe toxic side reactions occur, showing the complexity of difference in pharmacological function and determining great difference in the therapeutic index of single enantiomer and the racemate thereof. For example, the curative effect of well-known DL-(+−) syntomycin is half of D (−) chloramphenicol; the pharmaceutical activity of propranolol L-isomer is 100 times larger than that of D-isomer; (−) adanon is a strong painkiller while (+) is non-effective. There is also difference in toxicity. For example, the two enantiomers of thalidomide have similar sedation for mice, but only S (−) isomer and metabolin thereof have embryotoxin and teratogenesis; ketamine is a widely used anaesthetic and analgesic, but has side effects such as hallucinating. Studies show that S(+) is 3~4 times more effective than R(−) and toxic side effects have something to do with the latter. The great difference of chiral drug's curative effect has promoted the research and development of chiral drugs and the development separation analysis. By using "chiral" technology, we can remove those with no effect or toxic side effects from drugs effectively and produce pure chiral drugs with single and oriented structure, thus making more pure pharmaceutical ingredients, further quickening curative effect and shortening the course of treatment. Therefore, research on chiral drugs has become one of the new methods for new medicine research worldwide. National governments and pharmaceutical enterprises have invested heavily in fields such as preparations of chiral drug, chiral materials and chiral intermediate for research and development, for the purpose of seizing dominance of chiral pharmacy market. Beside, with continuous improvement of chiral technology, especially the fast and wide use of liquid chromatography, the separation analysis and determination of enantiomers of chiral drugs are promoted. Chiral drugs of single enantiomer have been widely used.

Through a lot of researches on whether carrimycin has optical activity too, the inventor is pleasantly surprised to find that by adjusting and optimizing the culturing and fermentation conditions, the inventor accidently gets a levocarrimycin with optical rotation, which has better anti-infection activity. Therefore, the present invention provides levocarrimycin, preparation methods thereof and uses in preparing drugs for preventing and treating infectious diseases.

SUMMARY OF THE INVENTION

The first object of the present invention is to provide levocarrimycin, which has optical rotation and better anti-infection activity at the same time.

The second object of the present invention is to provide a pharmaceutical composition, the pharmaceutical composition contains levocarrimycin with optical rotation provided by the present invention and pharmaceutically acceptable carrier.

The third object of the present invention is to provide a preparation method of levocarrimycin, the method is characterized by simplified production process and easy-to-control quality standard, and the prepared levocarrimycin has good effect, optical rotation and better anti-infection activity.

The fourth object of the present invention is to provide a uses of said levocarrimycin or said pharmaceutical composition of levocarrimycin for manufacturing a medicament for the treatment and prevention of infectious diseases. Especially, levocarrimycin or pharmaceutical composition of levocarrimycin has good effect in resistance to bacteria, chlamydia and mycoplasma and can be used as drugs for infectious diseases.

To realize the first object of the prevent invention, the following technical solutions are adopted:

A levocarrimycin, the levocarrimycin is a mixture of isovalerylspiramycin III, II and I as main components and contains certain content of isobutyrylspiramycin III and II, butyrylspiramycin III and II, propionylspiramycin III and II, as well as acetylspiramycin III and II, among them the content of the isovalerylspiramycin III is no less than 30 wt %, the total content of isovalerylspiramycin III, II and I is no less than 60 wt %, and the content of acylspiramycin is 80-98 wt %, preferably 85~98 wt %, further preferably 90~98 wt % and most preferably 95~98 wt %; the specific optical rotation of said levocarrimycin is $[\alpha]D=-52°\sim-57°$ in the solution of 0.02 g/ml chloroform at temperature of 25° C., preferably, −54°~−56° and further preferably, −55°.

The inventor has made a lot of researches on carrimycin. By adjusting and optimizing the culture and fermentation conditions, especially by strict controlling the pH during the fermentation with pH regulator, the curves of pH variation with time show three continuous phases and each phase satisfies certain formula respectively, thus the levocarrimycin with optical activity is obtained. The possible reason is that the content of components with optical activity changed under the fermentation conditions or the optical configuration changed under the fermentation conditions.

Determination method of the specific optical rotation of levocarrimycin in the present invention is: weigh levocarrimycin prepared of present invention precisely, add chloroform solution and dilute into solution of about 10 mg/ml; measure the optical rotation by using D line of sodium spectrum (589.3 nm) with a measuring length of 1 dm and a measuring temperature of 25° C. and using a verified polarimeter with accuracy of 0.0001°.

The melting range of levocarrimycin of the present invention is 112~122° C., preferably, 114~120° C., further preferably, 116~118° C.

The determination method of melting range is: put appropriate amount of dried product in a capillary tube for melting point determination; repeat the determination for 3 times and take the average.

The levocarrimycin of the present invention has optical rotation. According to modern pharmacological research, the difference of drug enantiomer's affinity with receptor caused by the difference of drug enantiomer's stereoselectivity leads to great difference in pharmacological action. In vivo and in vitro pharmacodynamic tests prove that the levocarrimycin of the present invention has good anti-infection effect and good pharmacological activity at the same time, thus providing a new drug for treating infectious diseases and laying a foundation for researching chiral pharmaceutical preparation of carrimycin.

In vivo and in vitro tests prove that the levocarrimycin of the present invention has high sensitivity and low drug resistance, Levocarrimycin not only is effective against drug-resistant *staphylococcus aureus*, but also has inestimable value for bacterial infection caused by antibiotic abuse. For example, methicillin-resistant *staphylococcus aureus* (MRSA), *Escherichia coli* infection caused by extended-spectrum βlactamase (ESBL), and infectious diseases caused by *clostridium difficile* (C-diff) are all due to antibiotic abuse and are expected to be controlled for the coming out of levocarrimycin.

The levocarrimycin also contains spiramycin III and other components, among them the content of spiramycin III is no more than 1.0%, and the total content of other components is 2.0~19 wt %, preferably 2.0~14.0 wt %, further preferably 2.0~9.0 wt % and most preferably 2.0~4.0 wt %. In the present invention, said other compositions contain at least 3 improved homologs of spiramycin.

Levocarrimycin of the present invention is a mixture of isovalerylspiramycin III, II and I as main components, among them said isovalerylspiramycin III is a crystal compound of levoisovalerylspiramycin III, said isovalerylspiramycin II is a crystal compound of levoisovalerylspiramycin II, or said isovalerylspiramycin I is a crystal compound of levoisovalerylspiramycin I;

when the isovalerylspiramycin III is a crystal compound with III of levoisovalerylspiramycin, said crystal compound measured by the X-ray powder diffraction with Cu—Kα ray has characteristic peaks of 2θ at 8.0°, 10.0°, 11.2°, 11.7°, 16.4°, 19.1°, 19.6°, 20.0°, 21.4°, 22.9°, 23.6° and 29.4°;

when the isovalerylspiramycin II is a crystal compound with II of levoisovalerylspiramycin, said crystal compound measured by the X-ray powder diffraction with Cu—Kα ray has characteristic peaks of 2θ at 10.0°, 11.6°, 16.4°, 17.3°, 19.1°, 21.2°, 22.1°, 22.7°, 26.4°, 26.9°, 27.5° and 31.5°;

when the isovalerylspiramycin I is a crystal compound with I of levoisovalerylspiramycin, said crystal compound measured by the X-ray powder diffraction with Cu—Kα ray has characteristic peaks of 2θ at 7.6°, 8.0°, 10.0°, 11.4°, 16.4°, 17.0°, 17.5°, 17.9°, 19.5°, 22.7°, 23.7° and 24.4°.

Through further research, the inventor finds that after purifying and separating the levocarrimycin, single compositions of isovalerylspiramycin III, II or I are obtained; recrystallize one of the compositions, and the crystal compound of isovalerylspiramycin III, II or I is obtained; mix one of the crystal compounds with levocarrimycin to get levocarrimycin, in which, the isovalerylspiramycin II, II or I is the crystal compound of levoisovalerylspiramycin III, II, or I. In vivo pharmacodynamic test proves that the pharmacological effect of levocarrimycin, in which, the isovalerylspiramycin III, II or I is crystal of levoisovalerylspiramycin III, II, or I is much better than that of pure levocarrimycin.

To realize the second object of the present invention, the following technical solutions are adopted:

A pharmaceutical composition of levocarrimycin in which the pharmaceutical composition of levocarrimycin contains said levocarrimycin and pharmaceutically acceptable carrier.

Among said pharmaceutical compositions of present invention, the content of the levocarrimycin is of safe and therapeutically effective amount and is 10~90 wt % of that of the pharmaceutical composition, preferably, 25~75 wt %, and further preferably, 40~60 wt %.

"Safe and therapeutically effective amount" as employed in the present invention means the enough amount of drugs, compounds, compositions, products or medicaments that could alleviate, reverse or treat diseases of human and other mammals and that have no severe harm to the tissues of mammals.

The terminology "Pharmaceutically acceptable carrier" of present invention refers to conventional drug carriers in the field of pharmacy, for example, diluents, excipients such as water, fillers such as starch and cane sugar; adhesives such as cellulose derivatives, alginate, gelatins and polyvinylpyrrolidone; moistening agent such as glycerol; disintegrants such as agar, calcium carbonate and sodium bicarbonate; absorption enhancer such as quaternary ammonium compound; surfactants such as hexadecanol; adsorptive carriers such as kaolin and bentonite; lubricants such as talcum powder, calcium stearate, Mg and polyethylene glycol. Besides, other adjuvants such as spices and sweeteners can also be added in the pharmaceutical composition.

Compositions of the prevent invention can be any of diluents, disintegrant, lubricants, filler, adhesive, humectants, absorption enhancer, surfactant, excipient of safe and therapeutically effective amount, or commonly used drug carrier of safe and therapeutically effective amount in this field.

The pharmaceutical composition of levocarrimycin in the present invention exists in preparations applicable for pharmaceutical purpose, and the preparations are liquid, solid, semisolid, or gas preparations.

The liquid preparations comprise injection, infusion solution, solution, mixture, sirup, tincture or colloid, The solid preparations comprise power injection, lyophilized powder injection, tablet, capsule, powder, granula, pill, sublimed preparation or pellicle;

The semisolid preparations comprise ointment, plaster, suppository, extract or gel; The gas ones comprise aerosol or spray.

The pharmaceutical composition of levocarrimycin in the prevent invention, among them the content of said levocarrimycin is 10~1500 mg per unit formulation, preferably, 100~1000 mg per unit formulation and further preferably, 200~500 mg per unit formulation.

To realize the third object of the prevent invention, the following solutions are adopted:

A preparation method for levocarrimycin, which includes culture, fermentation and extraction process, among them the culture and fermentation is: culture the cloned fungal strains WSP-195 produced by spiramycin containing 4″-isovaleryl transferase gene on an slant culture-medium, inoculate it in a seed medium, then inoculate it into fermentation medium after culturing, and control the fermentation process by pH regulator. Fermentation proceeds under the pH of 6.0~9.0, preferably, 6.0~8.0, and further preferably, 6.0~7.5. The variation curves for pH with time show three continuous phases, the first phase satisfies formula $y_1 = k_1 x_1 + 6.0$, where $0.0227 \leq k_1 \leq 0.1364$, $0 < x_1 \leq 22$; the second phase satisfies $y_2 = k_2 x_2 + b_2$, where $-0.0735 \leq k_2 \leq 0$, $6.5 < b_2 \leq 10.62$, $22 \leq x_2 \leq 56$; and the third phase satisfies formula $y_3 = k_3 x_3 + b_3$, where $0 \leq k_3 \leq 0.0078$, $6.06 \leq b_3 \leq 6.5$, $56 \leq x_3 \leq 120$.

In the present invention, by adjusting and optimizing the culture and fermentation conditions, especially by controlling the pH during the fermentation with pH regulator, the curves of pH variation with time show three continuous phases and each phase satisfies certain formula respectively, thus levocarrimycin with optical activity is obtained.

In the present invention, the fermentation process is key, the pH needs to be detected regularly during the whole fermentation process and is controlled by adding pH regulator, in which, the pH regulator is any one of or combination of glucose, citric acid, acetic acid, hydrochloric acid, ammonia water, sodium hydroxide or potassium hydroxide, preferably, glucose, citric acid, acetic acid, ammonia water or combination thereof; further preferably, glucose, ammonia water or combination thereof.

The preparation method of the present invention, in which the extraction process is: process the fermentation liquor with aluminum sulfate to obtain the filtrate, adjust pH to 8.5~9.0, extract with butyl acetate, wash the butyl acetate extract with non-saline water and 1% $NaH_2PO_4$ respectively, then extract with water of pH 2.0~2.5 to obtain aqueous extract, adjust the pH to 4.5~5.5, volatilize and eliminate the residual butyl acetate to obtain hydrous extract, filter and adjust the pH to 8.5~9.0, obtain precipitate, wash precipitate with purified water and dry it to obtain levocarrimycin.

In said preparation method of the present invention, said slant culture-medium contains 2% soybean cake meal, 1% glucose, 3% starch, 0.5% $CaCO_3$, 0.4% NaCl and 2% agar.

In said preparation method of the present invention, said seed medium contains 1.5% soybean cake meal, 3.0% starch, 0.4% NaCl, 0.5% CaCO$_3$, 0.3% peptone and 0.05% KH$_2$PO$_4$.

In said preparation method of the present invention, said fermentation medium contains 0.5% glucose, 6.0% starch, 0.5% yeast powder, 2.0% fish meal, 0.6% NH$_4$NO$_3$, 1.0% NaCl, 0.5% CaCO$_3$, 0.05% KH$_2$PO$_4$, 0.1% MgSO$_4$, 0.5% soybean oil and 0.02% defoaming agent.

In said preparation method of the present invention, the culture on the slant culture-medium lasts for 8~15 days at temperature of 28~38° C.

In said preparation method of the present invention, the culture on the seed medium lasts for 40-hours at temperature of 25~30° C.

In said preparation method of the present invention, the fermentation on the fermentation medium lasts for 72~120 hours at temperature of 26~30° C.

When the levocarrimycin contains the crystal of isovalerylspiramycin I, II or III, said preparation method also comprises the following steps:
   a) Separate and purify the levocarrimycin to obtain levoisovalerylspiramycin I, II or III;
   b) Recrystallize the levoisovalerylspiramycin I, II or III to obtain the crystal compound of levoisovalerylspiramycin I, II or III;
   c) Eliminate the acetonitrile in the residual levocarrimycin after separating and purifying levoisovalerylspiramycin I, II or III in step a) through rotary evaporation, then extract with 1 time amount of ethyl acetate, and eliminate the ethyl acetate in the extract through rotary evaporation to obtain paste sample; re-dissolve the obtained sample with petroleum ether, and eliminate the petroleum ether through rotary evaporation to obtain the levocarrimycin;
   d) Mix the crystal compound of levoisovalerylspiramycin I, II or III obtained in step b) with the levocarrimycin obtained in step c) to obtain the levocarrimycin, among which, the isovalerylspiramycin I, II or III is the crystal compound of levoisovalerylspiramycin I, II or III.

The preparation method of present invention, said separation and purification process in step a) is: Purify the levocarrimycin obtained in the preliminary separation with a preparative high performance liquid chromatography, prepare chromatographic column with ODS, use acetonitrile and ammonium acetate buffer solution as the mobile phase in a gradient elute; record the separated UV spectrogram through UV detection, and collect the target peaks of levoisovalerylspiramycin I, II or III components:
Chromatographic column: ODS preparative chromatographic column;
   Mobile phase: acetonitrile (A), 100 mM ammonium acetate solution (B);
Gradient condition: adopting linear gradient for 0~60 min, A is 25%~65%; and 61~90 min, A is 65%~90%;
Flow velocity: 260 mL/min;
Injection volume: 10 mL;
Sampling concentration: 0.5 g/mL;
Measurement wavelength: 231 nm;
Way of collecting: collection via UV triggering;
   Collect the sample of levoisovalerylspiramycin I according to the retention time 44.759 min of levoisovalerylspiramycin I; or collect the sample of isovalerylspiramycin II according to the retention time 43.34 min of isovalerylspiramycin II; or collect the sample of levoisovalerylspiramycin III according to the retention time 48.009 of levoisovalerylspiramycin III; then eliminate acetonitrile through rotary evaporation, extract with 1 time amount of ethyl acetate, and eliminate the ethyl acetate in the extract through rotary evaporation to obtain paste sample; re-dissolve the obtained sample with petroleum ether, and eliminate the petroleum ether through rotary evaporation to obtain the white solid powder of levoisovalerylspiramycin I, II or III.

The preparation method of the present invention, when the isovalerylspiramycin I is a crystal of levoisovalerylspiramycin I, the crystal is obtained through the following recrystallization process: dissolve the white solid powder of levoisovalerylspiramycin I in the mixed solvent of absolute methanol, absolute ethyl alcohol and anhydrous acetone, then add pure water while stirring, after that, reduce the temperature to 5° C. 15° C. while stirring continuously, to obtain the crystal of the levoisovalerylspiramycin I, in which, the volume ratio of ethyl acetate to absolute ethyl alcohol to anhydrous acetone in the mixed solvent is 1:0.1~10:0.5~1, preferably, 1:2~8:0.8~1;

Among them, the first preferred technical solution for the recrystallization of the crystal of levoisovalerylspiramycin I is: the volume of pure water added is 2~9 times of the sum of ethyl acetate, absolute ethyl alcohol and anhydrous acetone, preferably, 2.5~7.5 times; the speed in adding pure water is 4~10 ml/min, preferably, 6~8 ml/min.

The second preferred technical solution for the recrystallization of the crystal of levoisovalerylspiramycin I is: the volume ratio of ethyl acetate to absolute ethyl alcohol to anhydrous acetone in the mixed solvent is 1:0.1~10:0.5~1, preferably, 1:2~8:0.8~1.

The third preferred technical solution for the recrystallization of the crystal of levoisovalerylspiramycin I is: the stirring speed when adding pure water is 30~60 rpm, preferably, 45~60 rpm; after the pure water is added, the stirring speed is 10~30 rpm, preferably, 10~20 rpm.

The fourth preferred technical solution for the recrystallization of the crystal of levoisovalerylspiramycin I is: after pure water is added, the cooling speed is 1~3° C. per hour, preferably, 1~1.5° C. per hour.

When the isovalerylspiramycin II is a crystal of levoisovalerylspiramycin II, the crystal is obtained through the following recrystallization process: dissolve the white solid powder of levoisovalerylspiramycin II in the mixed solvent of absolute methanol, absolute ethyl alcohol and anhydrous acetone, then add pure water while stirring, after that, reduce the temperature to 5° C.~15° C. while stirring continuously, to obtain the crystal of the levoisovalerylspiramycin II, in which the volume ratio of absolute methanol to anhydrous acetone to absolute ethyl alcohol in the mixed solvent is 1:0.1~10:0.5~1, preferably, 1:2~8:0.8~1.

Among them, the first preferred technical solution for the recrystallization of the crystal of levoisovalerylspiramycin II is: the volume of pure water added is 2~9 times of the sum of absolute methanol, absolute ethyl alcohol and anhydrous acetone, preferably, 2.5~7.5 times; the speed in adding pure water is 4~10 ml/min, preferably, 6~8 ml/min.

The second preferred technical solution for the recrystallization of the crystal of levoisovalerylspiramycin II is: the volume ratio of absolute methanol to anhydrous acetone to absolute ethyl alcohol in the mixed solvent is 1:0.1~10:0.5~1, preferably, 1:2~8:0.8~1.

The third preferred technical solution for the recrystallization of the crystal of levoisovalerylspiramycin II is: the stirring speed when adding pure water is 30~60 rpm, preferably, 45~60 rpm; after the pure water is added, the stirring speed is 10~30 rpm, preferably, 10~20 rpm.

The fourth preferred technical solution for the recrystallization of the crystal of levoisovalerylspiramycin II is: after pure water is added, the cooling speed is 1~3° C. per hour, preferably, 1~1.5° C. per hour.

When the isovalerylspiramycin III is a crystal of levoisovalerylspiramycin III, the crystal compound is obtained through the following recrystallization process: dissolve the white solid powder of levoisovalerylspiramycin III in the mixed solvent of absolute methanol, absolute ethyl alcohol and anhydrous acetone, then add pure water while stirring, after that, reduce the temperature to 5° C.~15° C. while stirring continuously, to obtain the crystal compound of the levoisovalerylspiramycin III, in which the volume ratio of absolute methanol to absolute ethyl alcohol to anhydrous acetone in the mixed solvent is 1:0.1~10:0.5~1, preferably, 1:2~8:0.8~1.

Among them, the first preferred technical solution for the recrystallization of the crystal compound of levoisovalerylspiramycin III is: the volume of pure water added is 2~9 times of the sum of absolute methanol, absolute ethyl alcohol and anhydrous acetone, preferably, 2.5~7.5 times; the speed in adding pure water is 4~10 ml/min, preferably, 6~8 ml/min.

The second preferred technical solution for the recrystallization of the crystal compound of levoisovalerylspiramycin III is: the volume ratio of absolute methanol to absolute ethyl alcohol to anhydrous acetone in the mixed solvent is 1:0.1~10:0.5~1, preferably, 1:2~8:0.8~1.

The third preferred technical solution for the recrystallization of the crystal compound of levoisovalerylspiramycin III is: the stirring speed when adding pure water is 30~60 rpm, preferably, 45~60 rpm; after the pure water is added, the stirring speed is 10~30 rpm, preferably, 10~20 rpm.

The fourth preferred technical solution for the recrystallization of the crystal compound of levoisovalerylspiramycin III is: after pure water is added, the cooling speed is 1~3° C. per hour, preferably, 1~1.5° C. per hour.

In the present invention, said infectious diseases are these diseases caused by infection of gram-positive bacterium, *staphylococcus aureus, streptococcus pneumoniae, mycoplasma pneumoniae, chlamydia pneumoniae, ureaplasma urealyticum, Chlamydia trachomatis, pyogenic streptococcus, Micrococcus catarrhalis, gonococcus, bacillus influenzae, legionella* or *anaerobe*. The present invention further provides uses of said levocarrimycin and said pharmaceutical composition for manufacturing an antibacterial medicament, the bacteria include *streptococcus pneumoniae*, Group A *streptococcus*, pyogenic *streptococcus, enterococcus, staphylococcus aureus, S. epidermids, Catarrhal coccus, gonococcus, bacillus influenzae, escherichia coli, enterotoxigenic escherichia coli, enteropathogenic escherichia coli, enteroinvasive Escherichia coli, Pseudomonas aeruginosa, Klebsiella pneumoniae, bacillus proteus vulgaris, typhoid bacillus, acinetobacter, citrobacter, Serratia marcescens, S. Sonnei, Sh. flexneri, Tritirachium album; legionella* like *legionella pneumophila, legionella gormanii, legionella bozemanii, legionella dumoffii, legionella jordanis, and legionella micdadei*; anaerobe like *bacteroides fragilis, bacteroides thetaiotaomicron, bacteroides vulgatus, bacteroides distasonis, bacteroides prevotella, Prevotella asaccharolyticus, Prevotella oralis, Fusobacteriumnu cleatum, Fusobacterium russll, bifidobacteria, lactobacillus, peptostreptococcus, propionibacterium acnes, clostridium perfringens*, and yeast-like fungus.

Person skilled in the art usually know, that the amount of active components necessary for treatment changes with various factors, including the nature of disease and patient's age and condition, and is finally determined by the doctor. If the pharmaceutical compositions of levocarrimycin in the present invention is administered by unit dosage form, the content of the levocarrimycin is 10~1500 mg per unit dosage form, preferably, 100~1000 mg per unit dosage form and further preferably, 200ƒ500 mg per unit dosage form. The dose needed everyday can be administered by single dose or divided dose.

In vitro pharmacodynamic test proves that the active components in levocarrimycin or its pharmaceutical compositions provided by present invention have optical activity and excellent anti-infective effect. The active components not only have good antibacterial activity against gram-positive bacterium, especially *staphylococcus aureus* that is resistant to erythrocin, β-lactamase, *streptococcus pneumonia*, and pyogenic *streptococcus*, but also are effective against some negative bacteria such as *catarrhal coccus, gonococcus, bacillus influenzae*, some *legionella* and anaerobe, especially *mycoplasma pneumonia* and *chlamydia pneumonia*.

Compared with the prior art, the present invention has the following advantages:

1) The levocarrimycin of the present invention has optical rotation, however, according to the modern pharmacological research, the difference of drug enantiomer's affinity with receptor caused by the difference of drug enantiomer's stereoselectivity leads to great difference in pharmacological action. In vivo and in vitro pharmacodynamic tests prove that levocarrimycin of the present invention has excellent anti-infective effect and good pharmacological activity at the same time, thus providing a new drug for curing infectious diseases and laying a foundation for researching and developing chiral drugs of carrimycin; in vivo pharmacodynamic test shows that the levocarrimycin, in which the isovalerylspiramycin I, II or III is the crystal compound of levoisovalerylspiramycin I, II or III has better protection function for the curative effect of mice infected by 12 strains of bacteria;

2) The preparation method for levocarrimycin provided in the present invention, by adjusting and optimizing the culture and fermentation conditions, especially by controlling the pH during the fermentation with pH regulator, the curves of pH variation with time show three continuous phases and each phase satisfies certain formula respectively, thus the levocarrimycin with optical activity is obtained;

3) The preparation method for levocarrimycin provided in the present invention, which is featured by simplified production process, is suitable for large-scale industrial production.

DETAILED DESCRIPTION OF PREFERRED EXAMPLES

The followings are the examples of the present invention and these examples aim to further describe, rather than limit, the present invention.

Example 1

Preparation of Levocarrimycin

1) Culture and Fermentation

Figure 1:
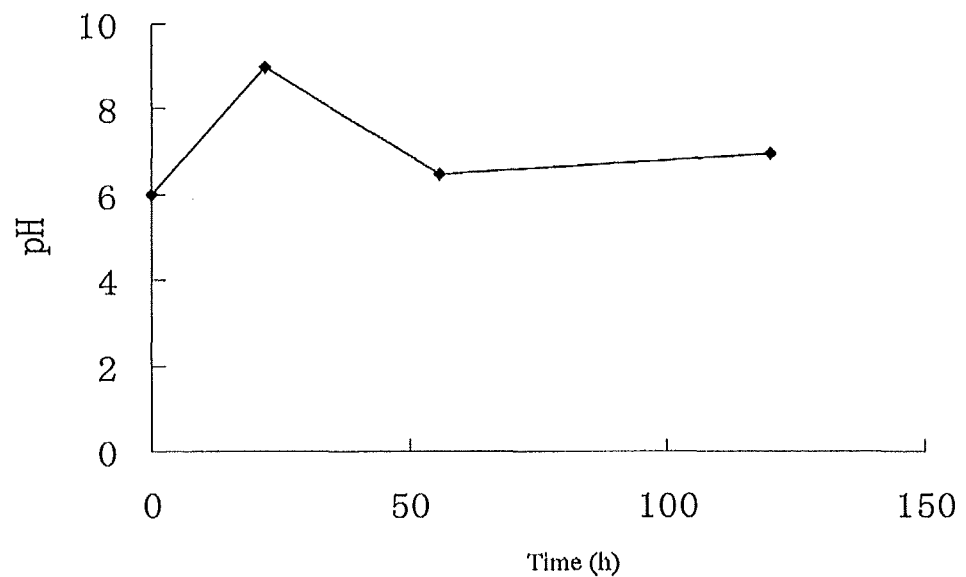
FIG. 1 is the variation curve of pH value-time during the fermentation in example 1 of the present invention.

Culture the cloned fungal strains WSJ-195 produced by spiramycin containing 4"-isovaleryl transferase gene on an slant culture-medium, inoculate it in seed medium, then inoculate it in fermentation medium after culturing, and control the fermentation process by glucose and ammonia water. The fermentation lasts for 120 h under the pH value is 6.0~9.0. The variation curves for pH with time show three continuous phases, the first phase satisfies formula $y_1=0.1364x_1+6.0$, where $0<x_1 \leq 22$; the second phase satisfies formula $y_2=-0.0735x_2+10.64$, where $22 \leq xhd\ 2 \leq 56$; the third phase satisfies formula $y_3=0.0078x_3+6.06$, where $56 \leq x_3 \leq 120$, see FIG. 1 for the variation curve, obtain the fermentation broth.

2) Extraction

Process the fermentation broth with aluminum sulfate to obtain filtrate, adjust the pH to 9.0, extract with butyl acetate, wash the butyl acetate extract with non-saline water and 1% $NaH_2PO_4$ respectively, then extract with pH 2.5 water to obtain aqueous extract, adjust the pH to 4.5, volatilize and eliminate the residual butyl acetate to obtain hydrous extract, filter and adjust the pH to 8.5, obtain precipitate, wash precipitate with purified water and dry it to obtain levocarrimycin.

Example 2

Preparation of Levocarrimycin

1) Culture and Fermentation

Figure 2:
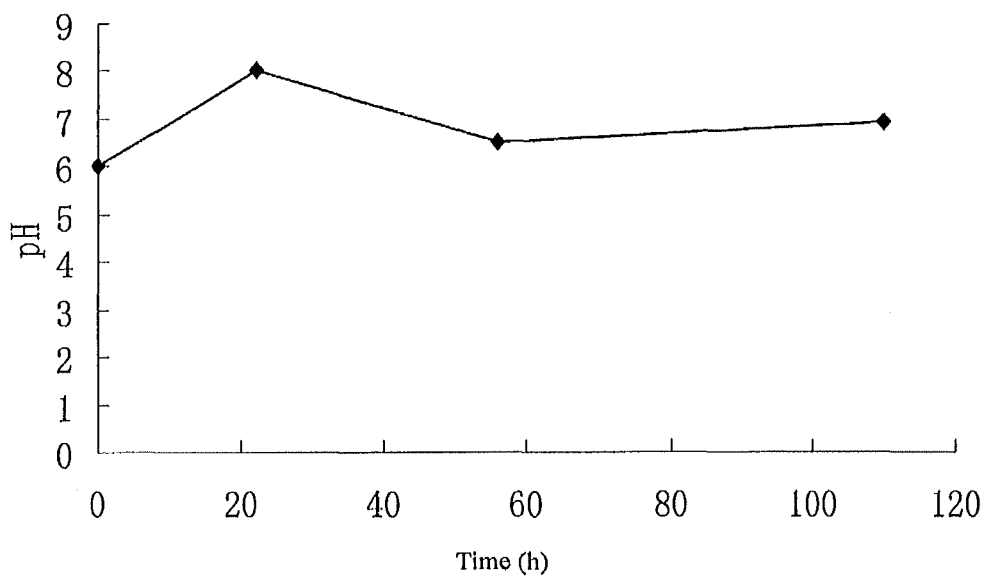
FIG. 2 is the variation curve of pH value-time during the fermentation in example 2 of the present invention.

Culture the cloned fungal strains WSJ-195 produced by spiramycin containing 4"-isovaleryl transferase gene on an slant culture-medium, inoculate it in seed medium, then inoculate it in fermentation medium after culture, and control the fermentation process by glucose and sodium hydroxide. The fermentation lasts for 110 h under the condition of the pH value is 6.0~8.0. The variation curves for pH with time show three continuous phases, the first phase satisfies formula $y_1=0.0909x_1+6.4$, where $0<x_1 \leq 22$; the second phase satisfies formula $y_2=-0.0441x_2+7.8$, where $22 \leq x_2 \leq 56$; and the third phase satisfies formula $y_3=0.0078x_3+6.06$, where $56 \leq x_3 \leq 110$, see FIG. 2 for the variation curve, obtain the fermentation broth.

2) Extraction

Process the fermentation broth with aluminum sulfate to obtain filtrate, adjust the pH to 8.9, extract with butyl acetate, wash the butyl acetate extract with non-saline water and 1% $NaH_2PO_4$ respectively, then extract with pH 2.2 water to obtain aqueous extract, adjust the pH to 4.2, volatilize and eliminate the residual butyl acetate to obtain hydrous extract, filter and adjust the pH to 8.5, obtain precipitate, wash precipitate with purified water and dry it to obtain levocarrimycin.

Example 3

Preparation of Levocarrimycin

1) Culture and Fermentation

Figure 3:
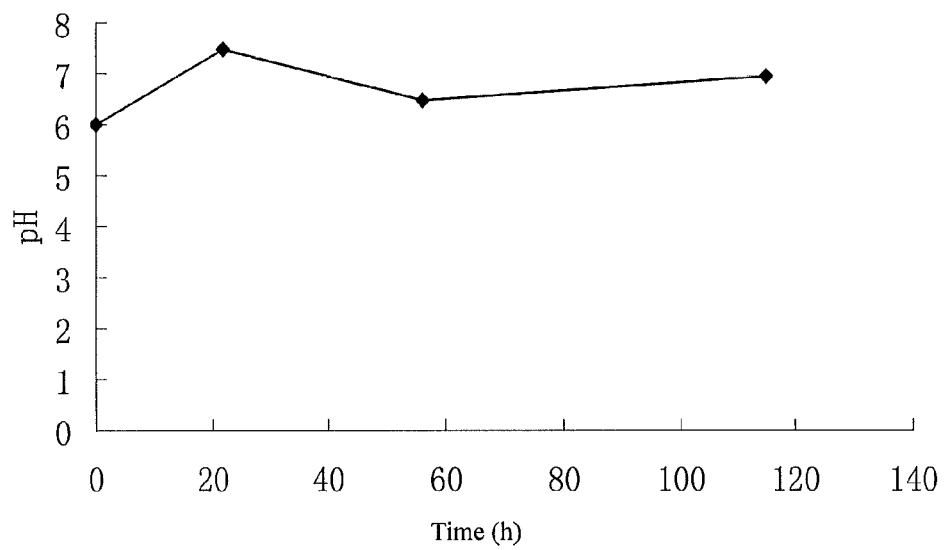
FIG. 3 is the variation curve of pH value-time during the fermentation in example 3 of the present invention.

Culture the cloned fungal strains WSJ-195 produced by spiramycin containing 4"-isovaleryl transferase gene on an slant culture-medium, inoculate it in seed medium, then inoculate in fermentation medium after culture, and control the fermentation process by glucose and citric acid. The fermentation lasts for 115 h under the condition of the pH value is 6.0~7.5. The variation curves for pH with time show three continuous phases, the first phase satisfies formula $y_1=0.0682x_1+6.0$, where $0<x_1<22$; the second phase satisfies formula $y_2=-0.0294x_2+8.147$, where $22<x_2<56$; the third phase satisfies formula $y_3=0.0078x_3+6.06$, where $56<x_3<115$, see FIG. 3 for the variation curve, obtain the fermentation broth.

2) Extraction

Process the fermentation broth with aluminum sulfate to obtain filtrate, adjust the pH to 8.6, extract with butyl acetate, wash the butyl acetate extract with non-saline water and 1% $NaH_2PO_4$ respectively, then extract with pH 2.3 water to obtain aqueous extract, adjust the pH to 5.2, volatilize and eliminate the residual butyl acetate to obtain hydrous extract, filter and adjust the pH to 8.7, obtain precipitate, wash precipitate with purified water and dry it to obtain levocarrimycin.

Example 4

Preparation of Levocarrimycin

1) Culture and Fermentation

Culture the cloned fungal strains WSJ-195 produced by spiramycin containing 4"-isovaleryl transferase gene on a slant culture-medium which containing 2% soybean cake meal, 1% glucose, 3% starch, 0.5% $CaCO_3$, 0.4% NaCl and 2% agar for 15 days at 28° C., inoculate it in a seed medium which containing 1.5% soybean cake meal, 3.0% starch, 0.4% NaCl, 0.5% $CaCO_3$, 0.3% peptone and 0.05% $KH_2PO_4$ for 80 hours at 25° C., then inoculate in a fermentation medium which containing 0.5% glucose, 6.0% starch, 0.5% yeast powder, 2.0% fish meal, 0.6% $NH_4NO_3$, 1.0% NaCl, 0.5% $CaCO_3$, 0.05% $KH_2PO_4$, 0.1% $MgSO_4$, 0.5% soybean oil and 0.02% defoamer with an inoculation size of 0.1%, and control the fermentation process by glucose and ammonia water. The fermentation lasts for 120 h under the pH value is 6.0~9.0. The variation curves for pH with time show three continuous phases, the first phase satisfies formula $y_1=0.1364x_1+6.0$, where $0<x_1 \leq 22$; the second phase satisfies formula $y_2=-0.0735x_2+10.64$, where $22 \leq x_2 \leq 56$; the third phase satisfies formula $y_3=0.0078x_3+6.06$, where $56 \leq x_3 \leq 120$, and the fermentation broth is obtained.

2) Extraction

Process the fermentation broth with aluminum sulfate to obtain filtrate, adjust the pH to 8.5, extract with butyl acetate, wash the butyl acetate extract with non-saline water and 1% $NaH_2PO_4$ respectively, then extract with pH 2.0 water to obtain aqueous extract, adjust the pH to 4.5, volatilize and eliminate the residual butyl acetate to obtain hydrous extract, filter and adjust the pH to 8.5 to obtain precipitate, wash precipitate with purified water dry it to obtain levocarrimycin.

Example 5

Preparation of Levocarrimycin

1) Culture and Fermentation

Culture the cloned fungal strains WSJ-195 produced by spiramycin containing 4"-isovaleryl transferase gene on a slant culture-medium which containing 2% soybean cake meal, 1% glucose, 3% starch, 0.5% $CaCO_3$, 0.4% NaCl and 2% agar for 8 days at 38° C., inoculate it in a seed medium which containing 1.5% soybean cake meal, 3.0% starch, 0.4% NaCl, 0.5% $CaCO_3$, 0.3% peptone and 0.05% $KH_2PO_4$ for 40 hours at 30° C., then inoculate in a fermentation medium which containing 0.5% glucose, 6.0% starch, 0.5% yeast powder, 2.0% fish meal, 0.6% $NH_4NO_3$, 1.0% NaCl, 0.5% $CaCO_3$, 0.05% $KH_2PO_4$, 0.1% $MgSO_4$, 0.5% soybean oil and 0.02% defoamer with an inoculation size of 20%, and control the fermentation process by glucose and ammonia water. The fermentation lasts for 115 h under the pH value is 6.0~7.5 at 30° C. The variation curves for pH with time show three continuous phases, the first phase satisfies formula $y_1=0.0682x_1+6.0$, where $0<x_1\leq22$; the second phase satisfies formula $y_2=-0.0294x_2+8.147$, where $22\leq x_2\leq56$; the third phase satisfies formula $y_3=0.0078x_3+6.06$, where $56\leq x_3\leq115$, see FIG. 3 for the variation curve, obtain the fermentation broth.

2) Extraction

Process the fermentation broth with aluminum sulfate to obtain filtrate, adjust the pH to 9.0, extract with butyl acetate, wash the butyl acetate extract with non-saline water and 1% $NaH_2PO_4$ respectively, then extract with pH 2.5 water to obtain aqueous extract, adjust the pH to 4.5-5.5, volatilize and eliminate the residual butyl acetate to obtain hydrous extract, filter and adjust the pH to 9.0, obtain precipitate, wash precipitate with purified water and dry it to obtain levocarrimycin.

Example 6

Preparation of Levocarrimycin

1) Culture and Fermentation

Culture the cloned fungal strains WSJ-195 produced by spiramycin containing 4"-isovaleryl transferase gene on a slant culture-medium which containing 2% soybean cake meal, 1% glucose, 3% starch, 0.5% $CaCO_3$, 0.4% NaCl and 2% agar for 12 days at 30° C., inoculate it in a seed medium which containing 1.5% soybean cake meal, 3.0% starch, 0.4% NaCl, 0.5% $CaCO_3$, 0.3% peptone and 0.05% $KH_2PO_4$ for 60 hours at 28° C., then inoculate in a fermentation medium which containing 0.5% glucose, 6.0% starch, 0.5% yeast powder, 2.0% fish meal, 0.6% $NH_4NO_3$, 1.0% NaCl, 0.5% $CaCO_3$, 0.05% $KH_2PO_4$, 0.1% $MgSO_4$, 0.5% soybean oil and 0.02% defoamer with an inoculation size of 10%, and control the fermentation process by glucose and ammonia water. The fermentation lasts for 90 h under the pH value is 6.0~7.5 at 28° C. The variation curves for pH with time show three continuous phases, the first phase satisfies formula $y_1=0.0682x_1+6.0$, where $0<x_1\leq22$; the second phase satisfies formula $y_2=-0.0294x_2+8.147$, where $22\leq x_2\leq56$; the third phase satisfies formula $y_3=0.0078x_3+6.06$, where $56\leq x_3\leq90$, see FIG. 3 for the variation curve, obtain the fermentation broth.

2) Extraction

Process the fermentation broth with aluminum sulfate to obtain filtrate, adjust the pH to 8.7, extract with butyl acetate, wash the butyl acetate extract with non-saline water and 1% $NaH_2PO_4$ respectively, then extract with pH 2.2 water to obtain aqueous extract, adjust the pH to 5.0, volatilize and eliminate the residual butyl acetate to obtain hydrous extract, filter and adjust the pH to 8.7, obtain precipitate, wash precipitate with purified water and dry it to obtain levocarrimycin.

Example 7

Preparation of Levocarrimycin

1) Culture and Fermentation

Culture the cloned fungal strains WSJ-195 produced by spiramycin containing 4"-isovaleryl transferase gene on a slant culture-medium which containing 2% soybean cake meal, 1% glucose, 3% starch, 0.5% $CaCO_3$, 0.4% NaCl and 2% agar for 10 days at 35° C., inoculate it in a seed medium which containing 1.5% soybean cake meal, 3.0% starch, 0.4% NaCl, 0.5% $CaCO_3$, 0.3% peptone and 0.05% $KH_2PO_4$ for 55 hours at 26° C., then inoculate in a fermentation medium which containing 0.5% glucose, 6.0% starch, 0.5% yeast powder, 2.0% fish meal, 0.6% $NH_4NO_3$, 1.0% NaCl, 0.5% $CaCO_3$, 0.05% $KH_2PO_4$, 0.1% $MgSO_4$, 0.5% soybean oil and 0.02% defoamer with an inoculation size of 15%, and control the fermentation process by glucose and ammonia water. The fermentation lasts for 115 h under the pH value is 6.0~7.5 at 27° C. The variation curves for pH with time show three continuous phases, the first phase satisfies formula $y_1=0.0682x_1+6.0$, where $0<x_1\leq22$; the second phase satisfies formula $y_2=-0.0294x_2+8.147$, where $22\leq x_2\leq56$; the third phase satisfies formula $y_3=0.0078x_3+6.06$, where $56\leq x_3\leq110$, see FIG. 3 for the variation curve, obtain the fermentation broth.

2) Extraction

Process the fermentation broth with aluminum sulfate to obtain filtrate, adjust the pH to 8.6, extract with butyl acetate, wash the butyl acetate extract with non-saline water and 1% $NaH_2PO_4$ respectively, then extract with pH 2.3 water to obtain aqueous extract, adjust the pH to 4.8, volatilize and eliminate the residual butyl acetate to obtain hydrous extract, filter and adjust the pH to 8.8, obtain precipitate, wash precipitate with purified water and dry it to obtain levocarrimycin.

Example 8

Preparation of Levocarrimycin

1) Culture and Fermentation

Culture the cloned fungal strains WSJ-195 produced by spiramycin containing 4"-isovaleryl transferase gene on a slant culture-medium which containing 2% soybean cake meal, 1% glucose, 3% starch, 0.5% $CaCO_3$, 0.4% NaCl and 2% agar for 13 days at 36° C., inoculate it in a seed medium which containing 1.5% soybean cake meal, 3.0% starch, 0.4% NaCl, 0.5% $CaCO_3$, 0.3% peptone and 0.05% $KH_2PO_4$, for 75 hours at 27° C., then inoculate in a fermentation medium which containing 0.5% glucose, 6.0% starch, 0.5% yeast powder, 2.0% fish meal, 0.6% $NH_4NO_3$, 1.0% NaCl, 0.5% $CaCO_3$, 0.05% $KH_2PO_4$, 0.1% $MgSO_4$, 0.5% soybean oil and 0.02% defoamer with an inoculation size of 0.5%, and control the fermentation process by glucose and ammonia water. The fermentation lasts for 98 h under the pH value is 6.0~8.0 at 29° C. The variation curves for pH with time show three continuous phases, the first phase satisfies formula $y_1=0.0909x_1+6.4$, where $0<x_1 \leq 22$; the second phase satisfies formula $y_2=-0.0441x_2+7.8$, where $22 \leq x_2 \leq 56$; the third phase satisfies formula $y_3=0.0078x_3+6.06$, where $56 \leq x_3 \leq 110$, see FIG. 2 for the variation curve, obtain the fermentation broth.

2) Extraction

Process the fermentation broth with aluminum sulfate to obtain filtrate, adjust the pH to 8.9, extract with butyl acetate, wash the butyl acetate extract with non-saline water and 1% $NaH_2PO_4$ respectively, then extract with pH 2.4 water to obtain aqueous extract, adjust the pH to 4.6, volatilize and eliminate the residual butyl acetate to obtain hydrous extract, filter and adjust the pH to 8.6 to obtain precipitate, wash precipitate with purified water and dry it to obtain levocarrimycin.

Example 9

HPLC Quantitative Determination Method of Levocarrimycin

Determine by high performance liquid chromatography (Appendix V D of Chinese Pharmacopoeia 2005 (2))

Adopt Venusil XBP C18 (L) 150 Å (200 mm×4.6 mm, Sum) chromatographic column (AGELA TECHNOLOGIES), mobile phase A is acetonitrile, mobile phase B is 0.01 mol·L$^{-1}$ ammonium acetate solution (adjust the pH value to 7.0 by ammonia water), gradient elution according to the following table; the wavelength is 232 nm, the flow rate is 1.0 mL·min$^{-1}$, the column temperature is 25° C. and the injection volume is 20 μl.

| Time (min) | Mobile phase A (%) | Mobile phase B (%) |
|---|---|---|
| 0 | 35 | 65 |
| 15 | 50 | 50 |
| 50 | 65 | 35 |
| 51 | 35 | 65 |
| 70 | 35 | 65 |

Figure 4:
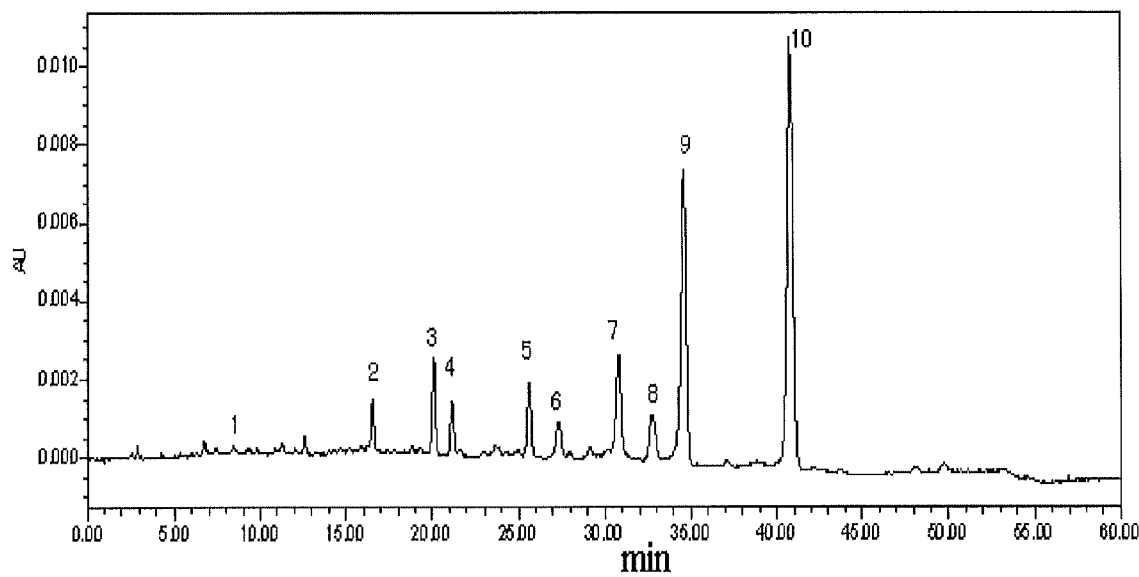
FIG. 4 is the liquid chromatogram of components of standard carrimycin, among them, 1—spiramycin III
2—monoacetyl spiramycin II
3—monoacetyl spiramycin III
4—propionylspiramycin II
5—propionylspiramycin III
6—(iso-) butyrylspiramycin II
7—isovalerylspiramycin I
8—(iso-) butyrylspiramycin III
9—isovalerylspiramycin II
10—isovalerylspiramycin III

The chromatographic condition and system suitability test shall refer to the liquid chromatogram of standard carrimycin component (FIG. 4). Adjusting the chromatographic condition and, if necessary, change the gradient elution condition of mobile phase to make the sample levocarrimycin component consistent with spectra of standard carrimycin component (FIG. 4).

Solution of standard sample: weigh proper amount of standard product accurately, dilute it by the mixed liquor of 0.01 mol/L ammonium acetate solution (adjust the pH value to 7.0 by ammonia water) and acetonitrile in a proportion of 65:35 to a concentration of 0.4 mg/ml-0.6 mg/ml as the solution of standard sample and shake well for future use.

Solution of testing sample: weigh 50 mg testing sample, dilute it by the mixed liquor of 0.01 mol/L ammonium acetate solution (adjust the pH value to 7.0 by ammonia water) and acetonitrile (proportion of 65 to 35) to 50 ml as the solution of sample product and shake well for future use. Calculate based on the peak area of isovalerylspiramycin III by external standard method. The isovalerylspiramycin III shall not be less than 30%, the isovalerylspiramycin (I+II+III) shall not be less than 60%; the total content of acylation spiramycin's 9 components shall not be less than 80%, the amount of spiramycin III shall not be more than 1.0% and the total content of other unknown components shall not be more than 5.0%. The calculation formula is shown as follows:

Isovalerylspiramycin III (%)=$A_{isovaleryl\ III} \times W_S \times P/(A_S \times W_T) \times 100\%$ Isovalerylspiramycin (I+II+III) (%)=$(A_{isovaleryl\ I} + A_{isovaleryl\ II} + A_{isovaleryl\ III}) \times W_S \times P/(A_S \times W_T) \times 100\%$ Total content of acylation spiramycin (%)= $(A_{acetyl\ II} + A_{Acetyl\ III} + A_{propionyl\ II} + A_{propionyl\ III} + A_{isobutyryl\ II} + A_{isovaleryl\ I} + A_{isobutyryl\ III} + A_{isovaleryl\ II} + A_{isovaleryl\ III}) \times W_S \times P/(A_S \times W_T) \times 100\%$ Spiramycin III (%)=$A_{spiral\ II} \times W_S \times P/(A_S \times W_T) \times 100\%$ Unknown components (%)=$A_W \times W_S \times P/(A_S \times W_T) \times 100\%$ Where:
$W_S$—weight of standard sample, g;
$A_S$—peak area of isovalerylspiramycin III in the standard sample;
$W_T$—weight of testing sample, g;
$A_W$—total peak area of unknown components in the testing sample;
P—purity of isovalerylspiramycin III in the testing sample.

Example 10

HPLC Detection of Levocarrimycin Component

Figure 5:
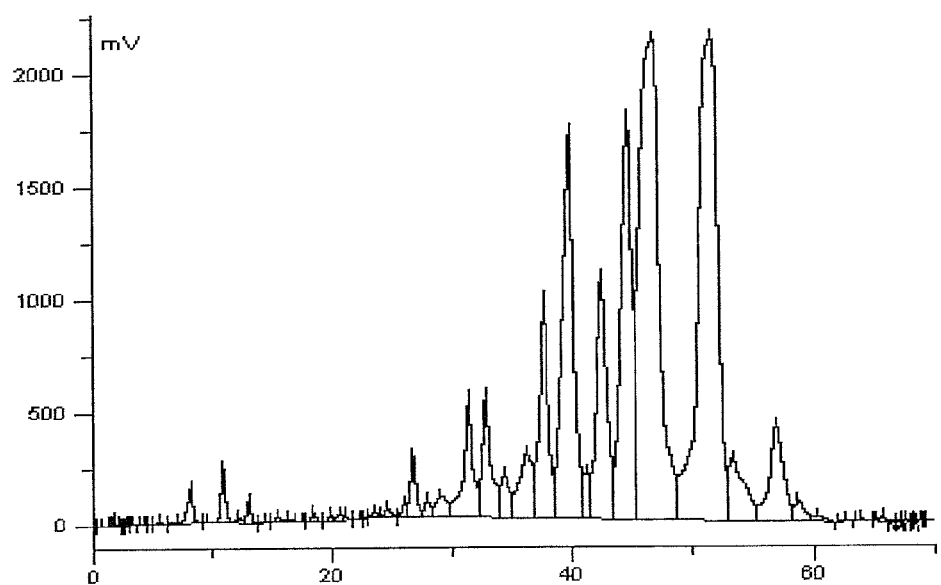
FIG. 5 is the liquid chromatogram of levocarrimycin provided in example 4 of the present invention.

Extract the eight batch fermentation broth of levocarrimycin fermented by the levocarrimycin extraction process provided in example 4 and the HPLC quantitative detection method provided in example 9, the HPLC detection conditions of each component obtained is shown as table 1 and the liquid chromatogram is shown as FIG. 5.

TABLE 1 the HPLC detection condition of eight batches levocarrimycin components

| Percentage content % | 1 | 2 | 3 | 4 | 5 | 6 | 7 | 8 | Average value |
|---|---|---|---|---|---|---|---|---|---|
| isv-III | 35.71 | 34.40 | 34.80 | 32.19 | 35.71 | 35.80 | 35.59 | 35.44 | 34.96 |
| isv-II | 24.67 | 24.93 | 24.36 | 24.85 | 20.02 | 23.91 | 23.87 | 23.76 | 23.80 |
| isv-I | 2.30 | 2.94 | 4.07 | 3.18 | 3.46 | 2.90 | 3.40 | 3.00 | 3.16 |
| bu-III | 3.56 | 2.75 | 3.54 | 3.50 | 3.50 | 3.90 | 4.10 | 4.00 | 3.61 |
| ibu-III | — | — | — | — | — | — | — | — | — |
| bu-II | 0.99 | 1.00 | | 1.15 | 1.07 | 1.20 | 1.30 | 1.20 | 0.99 |
| Ibu-II | — | — | — | — | — | — | — | — | — |
| pr-III | 7.91 | 8.09 | 7.65 | 8.19 | 8.24 | 8.40 | 8.70 | 8.50 | 8.21 |
| pr-II | 2.91 | 2.65 | 3.07 | 3.72 | 3.90 | 5.40 | 5.11 | 5.36 | 4.02 |

TABLE 1-continued the HPLC detection condition of eight batches levocarrimycin components

| Percentage content % | 1 | 2 | 3 | 4 | 5 | 6 | 7 | 8 | Average value |
|---|---|---|---|---|---|---|---|---|---|
| ac-III | 1.50 | 1.19 | 1.07 | 0.96 | 1.14 | 1.36 | 1.68 | 1.29 | 1.27 |
| ac-II | 2.84 | 2.92 | 3.05 | 3.08 | 3.47 | 1.89 | 3.18 | 3.09 | 2.94 |
| Total isv | 62.68 | 62.27 | 63.23 | 60.22 | 59.19 | 62.61 | 62.86 | 62.20 | 61.91 |
| Total acylation | 82.39 | 80.87 | 81.61 | 80.82 | 80.51 | 84.76 | 86.93 | 85.64 | 82.94 |

The above detection is also conducted for the levocarrimycin prepared in other examples in the present invention and the liquid chromatogram obtained is as shown in FIG. 5.

Example 11

Determination of Specific Rotation of Levocarrimycin

Precisely weigh a proper amount of levocarrimycin prepared in the examples of the present invention, add chloroform to dissolve and dilute into a solution of 0.02 g/ml chloroform, and determine the specific rotation with D line (589.3 nm) of natrium spectrum with a determination length of 1 dm, determination temperature of 25° C., polarimeter with reading to 0.0001° after being calibrated.

TABLE 2

Investigation result of specific rotation

| Example NO. | 1 | 2 | 3 | 4 | 5 | 6 | 7 | 8 |
|---|---|---|---|---|---|---|---|---|
| $[\alpha]^{25}$ | −52° | −55.2° | −57° | −56° | −54° | −55.3° | 55.1° | 55.4° |

Example 12

Levocarrimycin Tablets (Calculated in 10000 Tablets)

| Formulation: | Levocarrimycin raw powder provided by example 4 | 1000 g |
|---|---|---|
| | Low-substituted hydroxy propyl cellulose (5%) | 92.5 g |
| | Sodium carboxymethyl starch (3%) | 55.5 g |
| | Magnesium stearate (1%) | 18.5 g |
| | Starch | Total weight-weight of other raw adjuvant materials |
| | Total weight | 1850 g |

Preparation process: Weigh a proper amount of starch, dilute it to a concentration of 15%, heat it to a paste, and make into adhesive; make the main material carrimycin, adjuvant materials starch, low-substituted hydroxy propyl cellulose, sodium carboxymethyl starch and magnesium stearate pass through a 100-mesh sieve respectively, and weigh the needed main and adjuvant materials according to formulation; after mixing the carrimycin, starch, low-substituted hydroxy propyl cellulose uniformly, add starch paste of 15% starch concentration to make soft material, granulation with 14-mesh sieve, dry at 50-60° C., control the moisture at 3-5%, straighten granules with 14-mesh sieve, add sodium carboxymethyl starch, magnesium stearate and mix, then determine the content of granules; calculate the weight of every tablet according to content of granules, tablet (Φ9 mm retuse punch), detect differences of weight of tablets; package the qualified tablets after inspection.

Example 13

Levocarrimycin Capsules (Calculated in 10000 Capsules)

| Formulation: | Levocarrimycin raw powder in example 4 | 1000 g |
|---|---|---|
| | Starch (for pharmaceutical purpose) | 1080-weight of carrimycin raw powder |

-continued

| Pharmaceutical NO. 3 capsules | 1000 capsules |
|---|---|
| Liquid paraffin | 50 ml |

Preparation process: Respectively weigh the main material carrimycin and adjuvant material pharmaceutical starch according to the process formulation, add in a mixer for full mixing for 1.5-2 hours; the obtained data of the sample content tested shall be in basic accordance with theoretical data (weight in every capsule is about 0.105 g), respectively put the qualified pharmaceutical No. 3 capsules and the well-mixed raw materials into a filling machine according to operation requirements of the automatic capsule filling machine, conduct difference inspection for filled capsules (within ±10%, <0.3 g), and the dissolution shall meet the requirements; put the qualified capsules into a polishing machine and add liquid paraffin to conduct polishing for 15-20 min, and then take the capsules out and inspect the finished product packing boxes.

Example 14

Levocarrimycin Sugar-Coated Tablets (Calculated in 10000 Tablets)

Formula: Same as that of example 12

Preparation process: Operate as the method in example 12, put the qualified core tablets into a sugar-coating pot, slowly put the prepared syrup (concentration of 65-70%) into the pot, and then raise the temperature to about 40° C., add a proper amount of talcum, and conduct forced air drying for 20-30 min; after the tablets gain a sub-coat by repeating the above steps for several times, conduct sugar coating for 15-20 min; after the tablets gain a sugar coat put the prepared color paste into syrup and mix up, and then pour it into the pot and mix for 15-20 min every time to obtain the sugar-coated tablet.

Example 15

Levocarrimycin Dry Syrup (Calculated in 10000 Bags)

| Formulation: | Levocarrimycin raw powder in example 4 | 1250 g |
|---|---|---|
| | Citric acid (0.5%) (citrate) | 15 g |
| | Sucrose | Total weight-weight of other adjuvant materials |
| | Total weight | 500 g |
| | Pigment (curcumin) | about 1 g |

Preparation process: Respectively crush the carrimycin raw powder, citric acid, sucrose with a high-speed airflow crusher into granules in such a manner that 85% of which can pass through a 300-mesh sieve, and 15% pass through a 180-mesh sieve, respectively weigh a proper amount of the crushed fine powder according to the formulation and then mix them adequately for 1-1.5 hours; determine its content, calculate the packing volume (theoretical packing content is 500 mg every bag), and then put the mixture into a forming-filling-sealing machine, and pack it with aluminized paper. Pack the product according to the operation requirements of packaging machine, with the difference of packing content limited within +5%, inspect after packing, and then implement out packing for the qualified.

Example 16

Levocarrimycin Enteric-Coated Tablets (Calculated in 10000 Tablets)

Formulation: Refer to example 12.

Preparation process: prepare the tablet cores according to example 12; put the qualified tablet cores into a sugar coating pot, use 60-70% syrup and talcum powder to coat three base coating layers and then coat the isolation layer, add 10% zein alcohol solution, dry for 10-15 min with rollover method, and then drop diethyl phthalate, acetone, cellulose acetate phthalate and alcohol solution, i.e. the enteric-coated solution into the pot and dry for 2-3 times and 10-15 min of one time with rollover method; after conforming qualification in examination, conduct sugar coating according to example 7.

Example 17

Levocarrimycin Gastric-Coated Tablets (Calculated in 10000 Tablets)

Formulation: Refer to example 12.

Preparation process: prepare the tablet cores according to example 12; put the qualified tablet cores into a high-efficiency coating machine and then prepare the qualified coating powder (including fat soluble and water soluble) into coating solution according to the requirements and then put the coating solution into the colloid for crushing and filtering for use. Preheat the high-efficiency coating pot filled with tablet cores, with rotation speed controlled within 5-10 rpm and temperature of 45~60° C., spray the coating solution into the pot with aerosol sprayer (>300 meshes) and dry for 25-35 minutes, conduct the process repeatedly for 8-12 times, until the coating is uniform, and finally pack the qualified tablets after drying.

Example 18

Levocarrimycin Granules (Calculated in 10000 Bags)

| Formulation: | Levocarrimycin raw powder in example 5 | 1250 g |
|---|---|---|
| | Sugared powder | 20000 g |
| | Dextrin | 9000 g |
| | 5% PVP-K30 | Appropriate amount |

Preparation process: screen the carrimycin raw powder, powdered sugar and dextrin with a 120-mesh sieve, weigh carrimycin raw powder, powdered sugar and dextrin according to the formulation and mix them uniformly; made the above mixed uniform material into soft material with 5% PVP-K30 mucilage; prepare the material into granules with oscillating granulator, dry in 70° C., straighten granules, and then pack them after being inspected qualified.

Example 19

Levocarrimycin Freeze-Dried Powder Injection

Weigh 500 mg levocarrimycin raw powder prepared in example 6, mix it with adipic acid of equal mole, and then dissolve into 5 ml water to obtain light yellow transparent solution, with a pH value of 4.6~5.6. Add 40 mg mannitol as freeze-dried proppant, rapidly freeze for 9 h at a low temperature, and freeze-dried to obtain light yellow loose lump. Dissolve it with 10 ml sterile water before use.

Example 20

Levocanimycin Freeze-Dried Powder Injection

Weigh 500 mg levocarrimycin raw powder prepared in example 4, mix it with citric acid of equal mole, and then dissolve into 5 ml water to obtain light yellow transparent solution, with a pH value of 4.6~5.6. Add 40 mg mannitol as freeze-dried proppant, rapidly freeze for 9 h at a low temperature, and freeze-dried to obtain light yellow loose lump. Dissolve it with 10 ml sterile water before use.

Example 21

Levocarrimycin Freeze-Dried Powder Injection

Weigh 500 mg levocarrimycin raw powder prepared in example 5, mix it with maleic acid of equal mole, and then dissolve into 5 ml water to obtain light yellow transparent solution, with a pH value of 4.6~5.6. Add 40 mg mannitol as freeze-dried proppant, rapidly freeze for 9 h at a low temperature, and freeze-dried to obtain light yellow loose lump. Dissolve it with 10 ml sterile water before use.

Example 22

Figure 6:
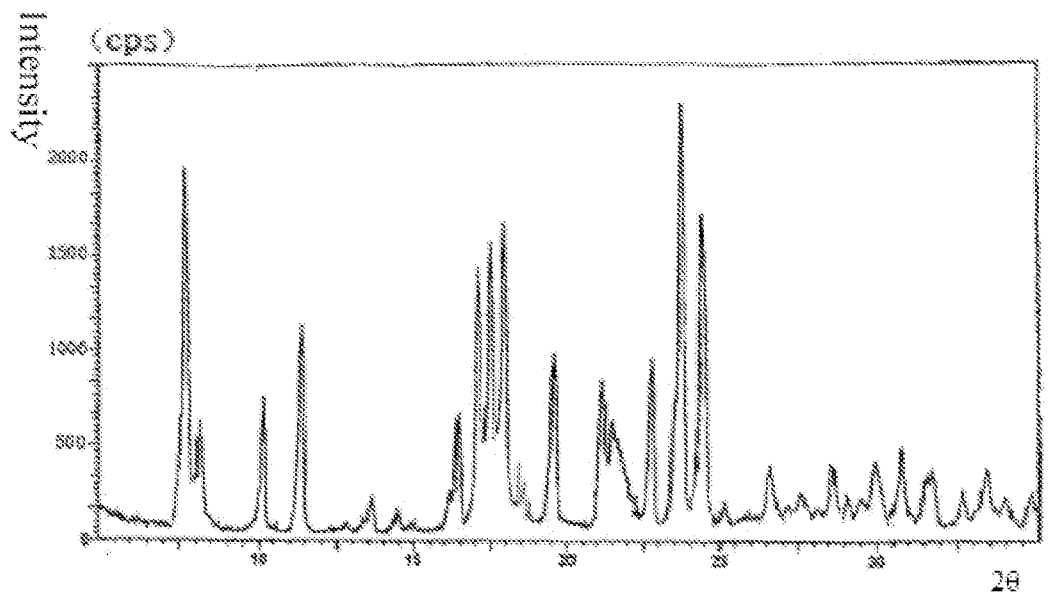
FIG. 6 is the X-ray powder diffraction pattern of crystal compound of levoisovalerylspiramycin I in the present invention.

Preparation of Levocarrimycin in which the Isovalerylspiramycin I is the Crystal Compound of Levoisovalerylspiramycin I Separate and purify levocarrimycin obtained in example 1. Purification of levoisovalerylspiramycin I: Purify the sample obtained in the preliminary separation with a preparative HPLC, prepare chromatographic column with ODS, use acetonitrile and ammonium acetate buffer solution as the mobile phase in a gradient elute; record the separated UV spectrogram through UV detection, and collect the target peaks of levoisovalerylspiramycin I components:
Chromatographic column: ODS preparative chromatographic column;
Mobile phase: Acetonitrile (A), 100 mM ammonium acetate solution (B);
Gradient condition: adopting linear gradient for 0~60 minutes, A is 25%~65%, and 61~90 minutes, A 65%-90%;
Flow velocity: 260 ml/min;
Injection volume: 10 mL;
Sampling concentration: 0.5 g/mL;
Measurement wavelength: 231 nm;
Way of collecting: collection via UV triggering;
Collect the sample of levoisovalerylspiramycin I according to the retention time (RT) 44.759 min of levoisovalerylspiramycin I, then eliminate acetonitrile through rotary evaporation, extract with 1 time amount of ethyl acetate, and eliminate the ethyl acetate in the extract through rotary evaporation to obtain paste sample; re-dissolve the paste sample with petroleum ether, and eliminate the petroleum ether through rotary evaporation to obtain the white solid powder of levoisovalerylspiramycin I.
Further recrystallize the white solid powder levoisovalerylspiramycin I to obtain the crystal compound. The method of recrystallization is as below:
(1) Dissolve the solid compound of levoisovalerylspiramycin I obtained in example 1 in the mixed solvent of ethyl acetate, absolute ethyl alcohol and anhydrous acetone, with the volume ratio of ethyl acetate to absolute ethyl alcohol to anhydrous acetone in the mixed solvent being 1:10:1;
(2) Then add pure water and stir the mixture simultaneously, and the volume of pure water added is 2.5 times of total volume of ethyl acetate, absolute ethyl alcohol and anhydrous acetone; the adding velocity of water is 4 ml/min; and the stirring rate when adding pure water is 30 rpm;
(3) Cool to 5° C. at a speed of 1° C./h after adding pure water, continue stirring at a speed of 10 rpm when cooling, to obtain the crystal compound of levoisovalerylspiramycin I.
The X-ray powder diffraction of the crystal compound of levoisovalerylspiramycin I measured by Cu—Kα X-ray has characteristic peaks of 2θ at 7.6°, 8.0°, 10.0°, 11.4°, 16.4°, 17.0°, 17.5°, 17.9°, 19.5°, 22.7°, 23.7° and 24.4°, and the spectrum of X-ray powder diffraction is as shown in FIG. 6.
Eliminate the acetonitrile in the residual levocarrimycin after separating and purifying levoisovalerylspiramycin I components through rotary evaporation, then extract with 1 time amount of ethyl acetate, and eliminate the ethyl acetate in the extract through rotary evaporation to obtain paste sample; re-dissolve the paste sample with petroleum ether, and eliminate the petroleum ether through rotary evaporation to obtain the levocarrimycin; then mix the levocarrimycin with the above crystal compound of levoisovalerylspiramycin I to obtain the levocarrimycin, in which the isovalerylspiramycin I is the crystal compound of levoisovalerylspiramycin I.

Example 23

Preparation of Levocarrimycin in which the Isovalerylspiramycin I is the Crystal Compound of Levoisovalerylspiramycin I Besides the steps which are the same as those in example 22, the difference in method of recrystallization is as below:
(1) Dissolve the solid compound of levoisovalerylspiramycin I in the mixed solvent of ethyl acetate, absolute ethyl alcohol and anhydrous acetone, with the volume ratio of ethyl acetate to absolute ethyl alcohol to anhydrous acetone in the mixed solvent being 1:10:1;
(2) Then add pure water and stir the mixture simultaneously, and the volume of pure water added is 9 times of total volume of ethyl acetate, absolute ethyl alcohol and anhydrous acetone; the adding velocity of water is 10 ml/min; and the stirring rate when adding pure water is 60 rpm;
(3) Cool to 15° C. at a speed of 3° C./h after addition of pure water, and continue stirring at a speed of 10 rpm when cooling, to obtain the crystal compound of levoisovalerylspiramycin I.
The X-ray powder diffraction of the crystal compound of levoisovalerylspiramycin I measured by Cu—Kα ray is similar to that of FIG. 6.

Example 24

The Preparation of Levocarrimycin in which the Isovalerylspiramycin I is the Crystal compound of Levolevoisovalerylspiramycin I Other operation steps are the same as example 22. What is different is the recrystallization, as follows:
1. First, dissolve the solid compound of levoisovalerylspiramycin I in the mixed solvent of ethyl acetate, absolute ethyl alcohol, and anhydrous acetone with the volume ratio of ethyl acetate to absolute ethyl alcohol to anhydrous acetone in the mixed solvent being 1:5:0.8;
2. Then add pure water and stir the mixture simultaneously, and the volume of pure water added is 7.5 times of the total volume of ethyl acetate, absolute ethyl alcohol, and anhydrous acetone; the adding velocity of water is 6 ml/min; and the stirring rate when adding pure water is 40 rpm;
3. Cool to 10° C. at a speed of 2° C./h after addition of pure water, and continue stirring at a speed of 15 rpm when cooling, to obtain the crystal compound of levoisovalerylspiramycin I.
Measured through Cu—Kα ray, the X-ray powder diffraction spectrum of the crystal compound of levoisovalerylspiramycin I is similar to that of FIG. 6.

Example 25

The Preparation of Levocarrimycin in which the Isovalcrylspiramycin I is the Crystal Compound of Levoisovalerylspiramycin I Other operation steps are the same as example 22. What is different is the recrystallization, as follows:
(1) First, dissolve the solid compound of levoisovalerylspiramycin I in the mixed solvent of ethyl acetate, absolute ethyl alcohol, and anhydrous acetone with the volume ratio of ethyl acetate to absolute ethyl alcohol to anhydrous acetone in the mixed solvent being 1:2:1;
(2) Then add pure water and stir the mixture simultaneously, and the volume of pure water added is 7.5 times of the total volume of ethyl acetate, absolute ethyl alcohol, and anhydrous acetone; the adding velocity of water is 8 ml/min; and the stirring rate when adding pure water is 45 rpm;
(3) Cool to 12° C. at a speed of 2.5° C./h after addition of pure water, and continue stirring at a speed of 20 rpm when cooling, to obtain the crystal compound of levoisovalerylspiramycin I.

Measured through Cu—Kα ray, the X-ray powder diffraction spectrum of the crystal compound of levoisovalerylspiramycin I is similar to FIG. 6.

Example 26

The Preparation of Levocarrimycin in which the Isovalerylspiramycin I is the Crystal Compound of Levoisovalerylspiramycin I Other operation steps are the same as example 22. What is different is the recrystallization, as follows:
(1) First, dissolve the solid compound of levoisovalerylspiramycin I in the mixed solvent of ethyl acetate, absolute ethyl alcohol, and anhydrous acetone with the volume ratio of ethyl acetate to absolute ethyl alcohol to anhydrous acetone in the mixed solvent being 1:5:0.8;
(2) Then add pure water and stir the mixture simultaneously, and the volume of pure water added is 5 times of the total volume of ethyl acetate, absolute ethyl alcohol, and anhydrous acetone; the adding velocity of water is 7 ml/minute; and the stirring rate when adding pure water is 60 revolutions/minutes;
(3) Cool to 12° C. at a speed of 1.2° C./h after addition of pure water, and continue stirring at a speed of 15 rpm when cooling, to obtain the crystal compound of levoisovalerylspiramycin I.

Measured through Cu—Kα ray, the X-ray powder diffraction spectrum of the crystal compound of levoisovalerylspiramycin I is similar to FIG. 6.

Example 27

The Preparation of Levocarrimycin in which the Isovalerylspiramycin II is the Crystal Compound of Levoisovalerylspiramycin II Purify the levocarrimycin obtained in example 2. The detailed operation steps are the same as example 22. What is different is the sample of levoisovalerylspiramycin II is collected according to the retention time RT 43.34 of levoisovalerylspiramycin II.

Further recrystallize the white solid powder levoisovalerylspiramycin II to obtain the crystal compound. The method of recrystallization is as below:
(1) First, dissolve the solid compound of levoisovalerylspiramycin II obtained in example 2 in the mixed solvent of absolute methanol, absolute ethyl alcohol, and anhydrous acetone with the volume ratio of absolute methanol to absolute ethyl alcohol to anhydrous acetone in the mixed solvent being 1:10:1;
(2) Then add pure water and stir the mixture simultaneously, and the volume of pure water added is 2.5 times of the total volume of absolute methanol, absolute ethyl alcohol, and anhydrous acetone; the adding velocity of water is 4 ml/min; and the stirring rate when adding pure water is 30 rpm;
(3) Cool to 5° C. at a speed of 1° C./h after addition of pure water, and continue stirring at a speed of 10 rpm when cooling, to obtain the crystal compound of levoisovalerylspiramycin II.

Figure 7:
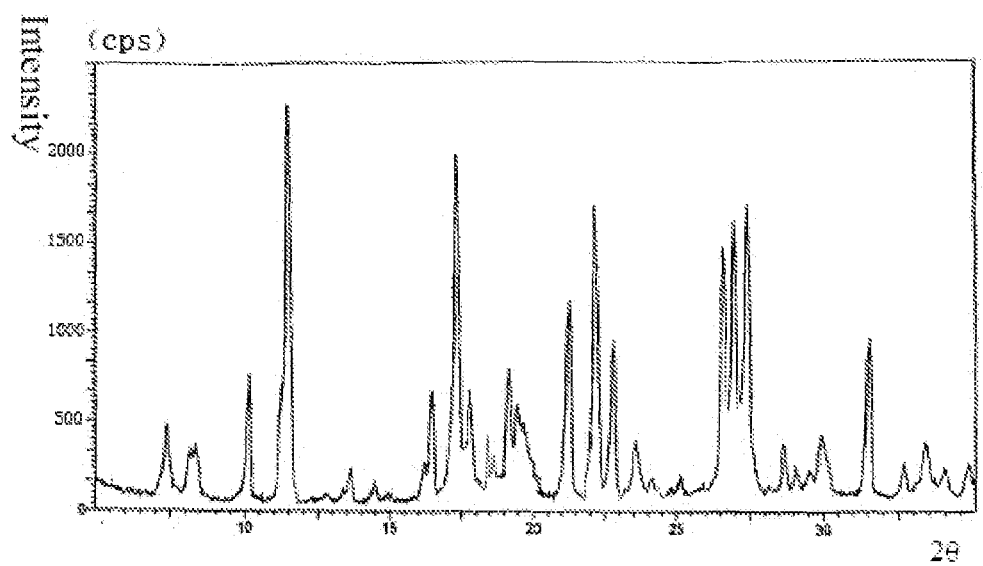
FIG. 7 is the X-ray powder diffraction pattern of crystal compound of levoisovalerylspiramycin II in the present invention.

The X-ray powder diffraction of the crystal compound of levoisovalerylspiramycin II measured by Cu—Kα X-ray has characteristic peaks of 2θ at 10.0°, 11.6°, 16.4°, 17.3°, 19.1°, 21.2°, 22.1°, 22.7°, 26.4°, 26.9°, 27.5°, and 31.5, and the spectrum of X-ray powder diffraction is as shown in FIG. 7. Eliminate acetonitrile of levocarrimycin which is purified and separated from the compositions of levoisovalerylspiramycin III through rotary evaporation, then extract the levocarrimycin with 1 times ethyl acetate, and eliminate ethyl acetate in the extract through rotary evaporation to obtain paste sample; redissolve the paste samples in petroleum ether, and then eliminate petroleum ether through rotary evaporation to obtain the levocarrimycin; then mix the levocarrimycin and the above crystal compound of levoisovalerylspiramycin II to make the levocarrimycin in which isovalerylspiramycin II is the crystal compound of levoisovalerylspiramycin II.

Example 28

The Preparation of Levocarrimycin in which the Isovalerylspiramycin II is the Crystal Compound of Levoisovalerylspiramycin II Other operation steps are the same as example 27. What is different is the recrystallization, as follows:
(1) First, dissolve the solid compound of levoisovalerylspiramycin II in the mixed solvent of absolute methanol, absolute ethyl alcohol, and anhydrous acetone with the volume ratio of absolute methanol to absolute ethyl alcohol to anhydrous acetone in the mixed solvent being 1:10:0.8;
(2) Then add pure water and stir the mixture simultaneously. The volume of pure water added is 9 times of the total volume of absolute methanol, absolute ethyl alcohol, and anhydrous acetone; the adding velocity of water is 10 ml/min; and the stirring rate when adding pure water is 60 rpm;
(3) Cool to 15° C. at a speed of 3° C./h after addition of pure water, and continue stirring at a speed of 10 rpm when cooling, to obtain the crystal compound of levoisovalerylspiramycin II.

Measured through Cu—Kα ray, the X-ray powder diffraction spectrum of the crystal compound of levoisovalerylspiramycin II is similar to FIG. 7.

Example 29

The Preparation of Levocarrimycin in which the Isovalerylspiramycin II is the Crystal Compound of Levoisovalerylspiramycin II Other operation steps are the same as example 27. What is different is the recrystallization, as follows:
(1) First, dissolve the solid compound of levoisovalerylspiramycin II in the mixed solvent of absolute methanol, absolute ethyl alcohol, and anhydrous acetone with the volume ratio of absolute methanol to absolute ethyl alcohol to anhydrous acetone in the mixed solvent being 1:5:1;
(2) Then add pure water and stir the mixture simultaneously. The volume of pure water added is 7.5 times of the total volume of absolute methanol, absolute ethyl alcohol, and anhydrous acetone; the adding velocity of water is 6 ml/min; and the stirring rate when adding pure water is 40 mp;

(3) Cool to 10° C. at a speed of 2° C./h after addition of pure water, and continue stirring at a speed of 15 rpm when cooling, to obtain the crystal compound of levoisovalerylspiramycin II.

Measured through Cu—Kα ray, the X-ray powder diffraction spectrum of the crystal compound of levoisovalerylspiramycin II is similar to FIG. 7.

Example 30

The Preparation of Levocarrimycin in which the Isovalerylspiramycin II is the Crystal Compound of Levoisovalerylspiramycin II Other operation steps are the same as example 27. What is different is the recrystallization, as follows:
(1) First, dissolve the solid compound of levoisovalerylspiramycin II in the mixed solvent of absolute methanol, absolute ethyl alcohol, and anhydrous acetone with the volume ratio of absolute methanol to absolute ethyl alcohol to anhydrous acetone in the mixed solvent being 1:3:1;
(2) Then add pure water and stir the mixture simultaneously. The volume of pure water added is 7.5 times of the total volume of absolute methanol, absolute ethyl alcohol, and anhydrous acetone; the adding velocity of water is 8 ml/min; and the stirring rate when adding pure water is 45 rpm;
(3) Cool to 12° C. at a speed of 2.5° C./h after addition of pure water, and continue stirring at a speed of 20 rpm when cooling, to obtain the crystal compound of levoisovalerylspiramycin II.

Measured through Cu—Kα ray, the X-ray powder diffraction spectrum of the crystal compound of levoisovalerylspiramycin II is similar to FIG. 7.

Example 31

The Preparation of Levocarrimycin in which the Isovalerylspiramycin II is the Crystal Compound of Levoisovalerylspiramycin II Other operation steps are the same as example 27. What is different is the recrystallization, as follows:
(1) First, dissolve the solid compound of levoisovalerylspiramycin II in the mixed solvent of absolute methanol, absolute ethyl alcohol, and anhydrous acetone with the volume ratio of absolute methanol to absolute ethyl alcohol to anhydrous acetone in the mixed solvent being is 1:6:0.8;
(2) Then add pure water and stir the mixture simultaneously. The volume of pure water added is 5 times of the total volume of absolute methanol, absolute ethyl alcohol, and anhydrous acetone; the adding velocity of water is 7 ml/min; and the stirring rate when adding pure water is 60 rpm;
(3) Cool to 12° C. at a speed of 1.2° C./h after addition of pure water, and continue stirring at a speed of 15 rpm when cooling, to obtain the crystal compound of levoisovalerylspiramycin II.

Measured through Cu—Kα ray, the X-ray powder diffraction spectrum of the crystal compound of levoisovalerylspiramycin II is similar to FIG. 7.

Example 32

The Preparation of Levocarrimycin in which the Isovalerylspiramycin III is the Crystal Compound of Levoisovalerylspiramycin III Purify the levocarrimycin made in example 3. The detailed operation steps are the same as example 22. Collect the samples of levoisovalerylspiramycin III in accordance with the retention time 48.009 of levoisovalerylspiramycin III.

Further recrystallize the white solid powder levoisovalerylspiramycin III to obtain the crystal compound. The method of recrystallization is as below:
(1) First, dissolve the solid compound of levoisovalerylspiramycin III made in example 3 in the mixed solvent of absolute methanol, absolute ethyl alcohol, and anhydrous acetone with the volume ratio of absolute methanol to absolute ethyl alcohol to anhydrous acetone in the mixed solvent being 1:10:1;
(2) Then add pure water and stir the mixture simultaneously, and the volume of pure water added is 2.5 times of the total volume of absolute methanol, absolute ethyl alcohol, and anhydrous acetone; the adding velocity of water is 4 ml/min; and the stirring rate when adding pure water is 30 rpm;
(3) Cool to 5° C. at a speed of 1° C./h after addition of pure water, and continue stirring at a speed of 10 rpm when cooling, to obtain the crystal compound of levoisovalerylspiramycin III.

Figure 8:
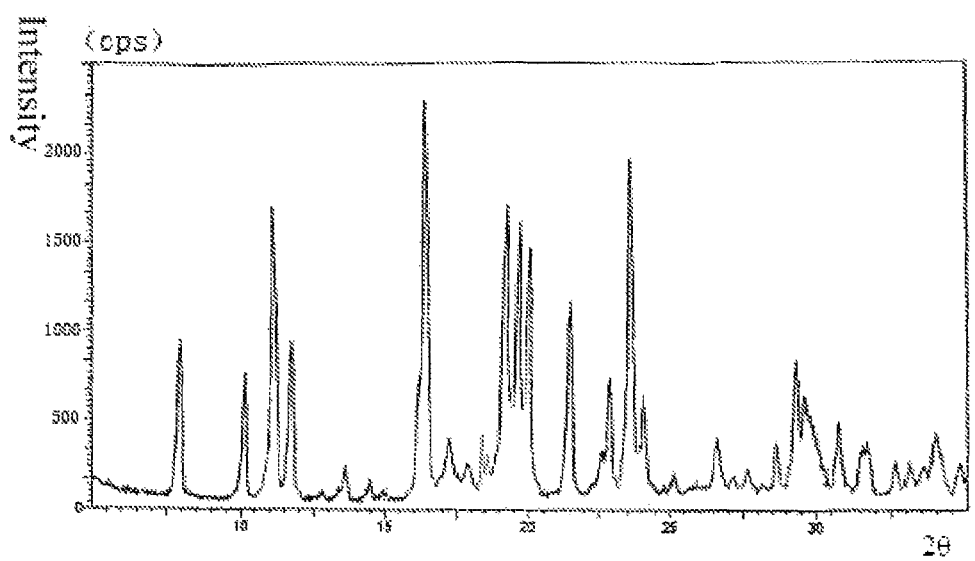
FIG. 8 is the X-ray powder diffraction pattern of crystal compound of levoisovalerylspiramycin III in the present invention.

The X-ray powder diffraction of the crystal compound of levoisovalerylspiramycin III measured by Cu—Kα X-ray has characteristic peaks of 2θ at 8.0°, 10.0°, 11.2°, 11.7°, 16.4°, 19.1°, 19.6°, 20.0°, 21.4°, 22.9°, 23.6°, and 29.4°, and the spectrum of X-ray powder diffraction is as shown in FIG. 8. Evaporate acetonitrile of levocarrimycin purified and separated from the compositions of the levoisovalerylspiramycin III through rotary evaporation, then extract the levocarrimycin with 1 times ethyl acetate, and evaporate ethyl acetate through rotary evaporation to obtain the paste samples; redissolve the paste samples in petroleum ether, and then evaporate the petroleum ether through rotary evaporation to obtain the levocarrimycin; then mix the levocarrimycin and the above crystal compound of levoisovalerylspiramycin III to obtain the levocarrimycin in which the isovalerylspiramycin III is the crystal compound of levoisovalerylspiramycin III.

Example 33

The Preparation of Levocarrimycin in which the Isovalerylspiramycin III is the Crystal Compound of Levoisovalerylspiramycin III Other operation steps are the same as example 32. What is different is the recrystallization, as follows:
(1) First, dissolve the solid compound of levoisovalerylspiramycin III in the mixed solvent of absolute methanol, absolute ethyl alcohol, and anhydrous acetone with the volume ratio of absolute methanol to absolute ethyl alcohol to anhydrous acetone in the mixed solvent being 1:10:1;
(2) Then add pure water with stirring. The volume of pure water added is 9 times of the total volume of absolute methanol, absolute ethyl alcohol, and anhydrous acetone; the adding velocity of water is 10 ml/min; and the stirring rate when adding pure water is 60 rpm;
(3) Cool to 15° C. at a speed of 3° C./h after addition of pure water, and continue stirring at a speed of 10 rpm when cooling, to obtain the crystal compound of levoisovalerylspiramycin III.

Measured through Cu—Kα ray, the X-ray powder diffraction spectrum of the crystal compound of levoisovalerylspiramycin III is similar to FIG. 8.

Example 34

Preparation of Levocarrimycin in which the Isovalerylspiramycin III is the Crystal Compound of Levoisovalerylspiramycin III Other operating steps are the same as example 32. The different ways of recrystallization are as follows:
(1) Dissolve the solid-state the compound of levoisovalerylspiramycin III into the mixed solvent which composed of absolute methanol, absolute ethyl alcohol and anhydrous acetone, and volume ratio of absolute methanol to absolute ethyl alcohol to anhydrous acetone in the mixed solvent is 1:5:0.8;
(2) Add pure water while stirring and the volume of added pure water is 7.5 times as much as the total volume of absolute methanol, absolute ethyl alcohol and anhydrous acetone; pure water will be added at the rate of 6 ml/min; the stirring rate for adding pure water is 40 rpm;
(3) Cool it down to 10° C. at the rate of 2° C./h after adding pure water, and keep stirring while cooling at the rate of 15 rpm; the crystal compound of levoisovalerylspiramycin III is obtained.

The X-ray powder diffraction patterns of the crystal compound of levoisovalerylspiramycin III measured by Cu—Kα ray are similar to FIG. 8.

Example 35

Preparation of Levocarrimycin in which the Isovalerylspiramycin III is the Crystal Compound of Levoisovalerylspiramycin III Other operating steps are the same as example 32, and the different ways of recrystallization are as follows:
(1) Dissolve the solid-state compound of levoisovalerylspiramycin III into the mixed solvent which composed of absolute methanol, absolute ethyl alcohol and anhydrous acetone, and volume ratio of absolute methanol to absolute ethyl alcohol to anhydrous acetone in the mixed solvent is 1:2:1;
(2) Add pure water while stirring and the volume of added pure water is 7.5 times as much as the total volume of absolute methanol, absolute ethyl alcohol and anhydrous acetone; pure water will be added at the rate of 8 ml/min; the stirring rate for adding pure water is 45 rpm;
(3) Cool it down to 12° C. at the rate of 2.5° C./h after adding pure water while stirring at the rate of 20 rpm, to obtain the crystal compound of levoisovalerylspiramycin III.

The X-ray powder diffraction patterns of the crystal compound of levoisovalerylspiramycin III measured by Cu—Kα ray are similar to FIG. 8.

Example 36

Preparation of Levocarrimycin in which the Isovalerylspiramycin III is the Crystal Compound of Levoisovalerylspiramycin III Other operating steps are the same as example 32, and the different ways of recrystallization are as follows:
(1) Dissolve the solid-state compound of levoisovalerylspiramycin III into the mixed solvent which composed of absolute methanol, absolute ethyl alcohol and anhydrous acetone, and volume ratio of absolute methanol to absolute ethyl alcohol to anhydrous acetone of the mixed solvent is 1:5:0.8;
(2) Add pure water while stirring and the volume of added pure water is 5 times as much as the total volume of absolute methanol, absolute ethyl alcohol and anhydrous acetone; pure water will be added at the rate of 7 ml/min; the stirring rate for adding pure water is 60 rpm;
(3) Cool it down to 12° C. at the rate of 1.2° C./h after adding pure water, while stirring at the rate of 15 rpm, to get the crystal compound of levoisovaleryispiramycin III.

The X-ray powder diffraction patterns of the crystal compound of levoisovalerylspiramycin III measured by Cu—Kα ray are similar to FIG. 8.

Example 37

Levocarrimycin Tablet Containing the Crystal Compound of Levoisovalerylspiramycin I The formulation and preparation method are the same as example 12. The difference is that the levocarrimycin powder is the levocarrimycin powder obtained in example 22, in which the isovalerylspiramycin I is the crystal compound of levoisovalerylspiramycin I.

Example 38

Levocarrimycin Tablet Containing the Crystal Compound of Levoisovalerylspiramycin II The formulation and preparation method are the same as example 12. The difference is that the levocarrimycin powder is the levocarrimycin powder obtained in example 27, in which the isovalerylspiramycin II is the crystal compound of levoisovalerylspiramycin II.

Example 39

Levocarrimycin Tablet Containing the Crystal Compound of Levoisovalerylspiramycin III The formulation and preparation method are the same as example 12. The difference is that the levocarrimycin powder is the levocarrimycin powder obtained in example 32, in which the sovalerylspiramycin IIII is the crystal compound of levoisovalerylspiramycin III.

Example 40

Levocarrimycin Capsule Containing the Crystal Compound of Levoisovalerylspiramycin I The formulation and preparation method are the same as example 13, the difference is that the levocarrimycin powder is the levocarrimycin powder obtained in example 23, in which the isovalerylspiramycin I is the crystal compound of levoisovalerylspiramycin I.

Example 41

Levocarrimycin Capsule Containing the Crystal Compound of Levoisovalerylspiramycin II The formulation and preparation method are the same as example 13. The difference is that the levocarrimycin powder is the levocarrimycin powder obtained in example 28, in which the isovalerylspiramycin II is the crystal compound of levoisovalerylspiramycin II.

Example 42

Levocarrimycin Capsule Containing the Crystal Compound of Levoisovalerylspiramycin III The formulation and preparation method are the same as example 13. The difference is that the levocarrimycin powder is the levocarrimycin powder obtained in example 33, in which the isovalerylspiramycin III is the crystal compound of levoisovalerylspiramycin III.

Adjuvant and preparation methods used for other preparations of levocarrimycin, in which the isovalerylspiramycin I, II or III is the crystal compound of levoisovalerylspiramycin I, II or III are the same as above.

Test Example 1

In Vivo Pharmacodynamic

Test method: infectious bacteria liquid preparation: put the bacteria liquid stored in the −80° C. refrigerator into the room for about 1 h at room temperature, and respectively draw 0.1 ml bacteria liquid of *streptococcus pneumonia, streptococcus pyogenes* and *enterococcus* into 2 ml MH soup (add 10% inactivated horse serum); inoculate the 2 ml MH soup with 0.1 ml bacteria liquid of *staphylococcus aureus* according to the above method, place the liquid into 37° C. incubator for 18 h to get the original bacteria liquid, dilute the original bacteria liquid with 5% gastric mucin, take 100% lethal bacteria amount if animal gets infected as infectious bacteria liquid.

Oral administration is planned for clinical medication of levocarrimycin, thus intragastric administration is selected for levocarrimycin test. After intraperitoneal injection of 0.5 ml lethal bacterial amount to the mice' abdominal cavity, the mice appear following symptom, such as reduced activity, repose, hair became loose, and so on. Clyster with 0.2 ml for every mouse after infection 0.5-6 h, there is no adverse reaction. Observe animal fatality within seven days and calculate the half protective dose (EDO of drugs for infected mice and compare the protective effect of drugs throuɡe Bliss order.

In vivo test results are as shown in table 3 and 4

TABLE 3

Comparison of curative effect of four antibiotics to the mice which abdominal cavity was infected by 6 strains *streptococcus*

| Test organism | Challenging dose (CFU/0.5 ml/mouse) | Drugs | MIC (µg/ml) | $ED_{50}$ (mg/kg) |
|---|---|---|---|---|
| *Streptococcus pneumonia*$_3$ | $6.4 \times 10^4$ | Carrimycin | 0.12 | 10.41 |
| | | Isovaleryl I is a crystal compound | 0.12 | 8.99 |
| | | Isovaleryl II is a crystal compound | 0.12 | 8.39 |
| | | Isovaleryl III is a crystal compound | 0.12 | 8.99 |
| | | Azithromycin | 0.5 | 18.29 |
| | | Acetyl spiramycin | 0.5 | 66.96 |
| | | Erythrocin | 1 | 85.08 |
| *Streptococcus pneumonia*$_{18}$ | $9.6 \times 10^4$ | Carrimycin | 0.03 | 10.06 |
| | | Isovaleryl I is a crystal compound | 0.03 | 9.94 |
| | | Isovaleryl II is a crystal compound | 0.03 | 9.08 |
| | | Isovaleryl III is a crystal compound | 0.03 | 8.98 |
| | | Azithromycin | 0.06 | 14.87 |
| | | Acetyl spiramycin | 0.06 | 37.93 |
| | | Erythrocin | 0.06 | 57.08 |
| *Streptococcus pneumonia*$_{57}$ | $8.8 \times 10^4$ | Carrimycin | 0.12 | 16.02 |
| | | Isovaleryl I is a crystal compound | 0.06 | 13.60 |
| | | Isovaleryl II is a crystal compound | 0.06 | 13.86 |
| | | Isovaleryl III is a crystalline compound | 0.06 | 12.81 |
| | | Azithromycin | 0.25 | 19.66 |
| | | Acetyl spiramycin | 1 | 398.01 |
| | | Erythrocin | 0.25 | 102.33 |

TABLE 3-continued

Comparison of curative effect of four antibiotics to the mice which abdominal cavity was infected by 6 strains *streptococcus*

| Test organism | Challenging dose (CFU/0.5 ml/mouse) | Drugs | MIC (µg/ml) | $ED_{50}$ (mg/kg) |
|---|---|---|---|---|
| *Streptococcus pyogenes*$_{772}$ | $6.9 \times 10^3$ | Carrimycin | 0.12 | 26.30 |
| | | Isovaleryl I is a crystalline compound | 0.06 | 26.15 |
| | | Isovaleryl II is a crystal compound | 0.06 | 23.37 |
| | | Isovaleryl III is a crystal compound | 0.06 | 23.37 |
| | | Azithromycin | 0.25 | 46.89 |
| | | Acetyl spiramycin | 0.25 | 98.11 |
| | | Erythrocin | 0.5 | 101.33 |
| *Streptococcus pyogenes*$_{102}$ | $7.8 \times 10^4$ | Carrimycin | 0.25 | 87.84 |
| | | Isovaleryl I is a crystal compound | 0.12 | 69.67 |
| | | Isovaleryl II is a crystal compound | 0.12 | 64.10 |
| | | Isovaleryl III is a crystal compound | 0.12 | 64.10 |
| | | Azithromycin | 0.5 | 159.06 |
| | | Acetyl spiramycin | 0.5 | 227.07 |
| | | Erythrocin | 0.5 | 361.01 |
| *Streptococcus pyogenes*$_{119}$ | $4.9 \times 10^4$ | Carrimycin | 0.25 | 68.48 |
| | | Isovaleryl I is a crystal compound | 0.12 | 61.87 |
| | | Isovaleryl II is a crystal compound | 0.12 | 59.91 |
| | | Isovaleryl III is a crystal compound | 0.12 | 59.91 |
| | | Azithromycin | 0.5 | 98.98 |
| | | Acetyl spiramycin | 0.5 | 117.53 |
| | | Erythrocin | 0.5 | 233.72 |

TABLE 4

Comparison of curative effect of 4 antibiotics to mice's abdominal cavity infected by *enterococcus* and *staphylococcus aureus*

| Test organism | Challenging dose (CFU/0.5 ml/mouse) | Drugs | MIC (µg/ml) | $ED_{50}$ (mg/kg) |
|---|---|---|---|---|
| *Enterococcus*$_{32}$ | $5.4 \times 10^4$ | Carrimycin | 0.5 | 89.29 |
| | | Isovaleryl I is a crystal compound | 0.5 | 85.15 |
| | | Isovaleryl II is a crystal compound | 0.25 | 68.54 |
| | | Isovaleryl III is a crystal compound | 0.25 | 68.54 |
| | | Azithromycin | 1 | 146.51 |
| | | Acetyl spiramycin | 1 | 130.34 |
| | | Erythrocin | 2 | 175.23 |
| *Staphylococcus aureus*$_{16}$ | $5.2 \times 10^3$ | Carrimycin | 0.5 | 31.98 |
| | | Isovaleryl I is a crystal compound | 0.5 | 25.97 |
| | | Isovaleryl II is a crystal compound | 0.25 | 26.02 |
| | | Isovaleryl III is a crystal compound | 0.25 | 26.02 |
| | | Azithromycin | 1 | 75.80 |
| | | Acetyl spiramycin | 1 | 43.58 |
| | | Erythrocin | 1 | 82.36 |
| *Staphylococcus aureus*$_{76}$ | $5.8 \times 10^4$ | Carrimycin | 0.5 | 31.50 |
| | | Isovaleryl I is a crystal compound | 0.5 | 26.50 |
| | | Isovaleryl II is a crystal compound | 0.25 | 25.16 |
| | | Isovaleryl III is a crystal compound | 0.25 | 25.16 |

TABLE 4-continued

Comparison of curative effect of 4 antibiotics to mice's abdominal cavity infected by enterococcus and staphylococcus aureus

| Test organism | Challenging dose (CFU/0.5 ml/mouse) | Drugs | MIC (µg/ml) | $ED_{50}$ (mg/kg) |
|---|---|---|---|---|
| | | Azithromycin | 1 | 58.79 |
| | | Acetyl spiramycin | 1 | 66.63 |
| | | Erythrocin | 1 | 64.17 |
| Staphylococcus aureus$_{12}$ | $4.8 \times 10^4$ | Carrimycin | 2 | 120.35 |
| | | Isovaleryl I is a crystal compound | 1 | 114.53 |
| | | Isovaleryl II is a crystal compound | 1 | 109.59 |
| | | Isovaleryl III is a crystal compound | 1 | 109.59 |
| | | Azithromycin | 4 | 217.36 |
| | | Acetyl spiramycin | 2048 | >500 |
| | | Erythrocin | 256 | 266.11 |
| Staphylococcus aureus$_{21}$ | $4.2 \times 10^4$ | Carrimycin | 1 | 59.30 |
| | | Isovaleryl I is a crystal compound | 0.5 | 42.67 |
| | | Isovaleryl II is a crystal compound | 0.5 | 47.65 |
| | | Isovaleryl III is a crystal compound | 0.5 | 47.65 |
| | | Azithromycin | 4 | 142.99 |
| | | Acetyl spiramycin | 2048 | >500 |
| | | Erythrocin | 4 | 213.67 |

In vivo test results indicate that: the curative effect of levocarrimycin to mice infected by 12 strains bacteria as shown in table 3 and 4, the results shows that it has good protective effect; and the levocarrimycin in which the isovalerylspiramycin I, II or III is the crystal compound of levoisovalerylspiramycin I, II or III shows better protective effect.

The same test is also conducted on the levocarrimycin or levocarrimycin preparations prepared in other examples of the present invention and the results are similar.

Test Example 2

In Vitro Pharmacodynamics

Determination of Clinical Isolates:

Test method: adopt two-fold plate dilution methods: pour the quantitative melted agra culture-medium into the plate which contains series drug concentration to mix with the liquid (add 5% fiber-free goat blood into streptococcus and enterococcus to get blood basal medium and add 7% fiber-free goat blood into bacillus influenzae and gonococcus medium to get chocolate basal medium), dilute the fresh-cultivated bacteria liquid into 106 CFU/ml after solidification, inoculate the cuvette agar of the levocarrimycin obtained from example 4 and control group of azithromycin, acetyl spiramycin and erythrocin through multipoint inoculating device, culture them under 37° C. for 18 h; put the gonococcus in an incubator of 5% $CO_2$ for 24 h; put legionella into an incubator of 5% $CO_2$ for 48 h; place anaerobe into an anaerobic box of 37° C. for 48 h. Observe that the minimum concentration of antibacterial drug that inhibits the growth of bacteria is the minimal inhibitory concentration (MIC) and calculate drugs $MIC_{50}$ and $MIC_{90}$ to be compared with the control drugs.

Notes:
$MIC_{50}$ inhibits 50% minimum Inhibitory concentration for the growth of bacteria;
$MIC_{90}$ inhibits 90% minimum Inhibitory concentration for the growth of bacteria.

Test results are as shown in the following table:

TABLE 5

Sensitive distribution of clinical isolates by carrimycin

| Strain and number of strain | Drugs | MIC scope (µg/ml) | $MIC_{50}$ (µg/ml) | $MIC_{90}$ (µg/ml) |
|---|---|---|---|---|
| Streptococcus pneumonia (112) | Carrimycin | 0.005->64 | 0.12 | 4 |
| | Azithromycin | 0.005->64 | 0.25 | 8 |
| | Acetyl spiramycin | 0.005->64 | 0.12 | >64 |
| | Erythrocin | 0.005->64 | 0.25 | 64 |
| Streptococcus pyogenes (93) | Carrimycin | 0.06->64 | 0.25 | 64 |
| | Azithromycin | 0.25->64 | 0.5 | >64 |
| | Acetyl spiramycin | 0.005->64 | 0.25 | >64 |
| | Erythrocin | 0.06->64 | 0.5 | >64 |
| Enterococcus (106) | Carrimycin | 0.5->64 | 2 | 64 |
| | Azithromycin | 0.25->64 | 8 | >64 |
| | Acetyl spiramycin | 0.12->64 | 4 | >64 |
| | Erythrocin | 0.5->64 | 4 | >64 |
| Staphylococcus aureus (155) | Carrimycin | 0.06->64 | 2 | 64 |
| | Azithromycin | 0.5->64 | 2 | >64 |
| | Acetyl spiramycin | 0.12->64 | 64 | >64 |
| | Erythrocin | 0.12->64 | 1 | >64 |
| Staphylococcus epidermidis (115) | Carrimycin | 0.12->64 | 2 | >64 |
| | Azithromycin | 0.12->64 | 8 | >64 |
| | Acetyl spiramycin | 0.03->64 | 64 | >64 |
| | Erythrocin | 0.06->64 | 8 | >64 |
| Bacillus influenzae (37) | Carrimycin | 0.03-32 | 0.12 | 1 |
| | Azithromycin | 0.03->64 | 0.25 | 2 |
| | Acetyl spiramycin | 0.03->64 | 0.12 | 4 |
| | Erythrocin | 0.03->64 | 0.06 | 32 |
| Gonococcus (10) | Carrimycin | 0.12-16 | 2 | 8 |
| | Azithromycin | 0.12-64 | 2 | 8 |
| | Acetyl spiramycin | 0.12-64 | 4 | 8 |
| | Erythrocin | 0.12-64 | 1 | 8 |

The same test is also conducted on levocarrimycin or levocarrimycin preparations prepared in other examples of the present invention and the results are similar.

Test Example 3

Determination of In Vitro Anti-chlamydia trachomatis and chlamydia pneumoniae Test Methods:
1. Cultivate HEp-2 and McCoy cell line in a 96-pore cell culture plate (Costar Company) respectively, 37° C. and 5% $CO_2$, for 48 h to make monolayer cells.
2. Dilute the bacteria to 10000~20000 ifu (inclusion bodies forming unit)/ml, adopt 0.1 ml/pore inoculation. Inoculate the McCoy cell culture plate with chlamydia trachomatis serotype B/TW-5/OT and D/UW-3/Cx and inoculate the HEp-2 cell culture plate with chlamydia pneumoniae CWL-029. Firstly, suck the cell culture liquid in the 96-pore cell culture plate, and then inocultate the plate by 0.1 ml/pore. Among them, do not inoculate 4 pores of A11~D11 and 2 pores of C12 and D12 with bacteria.
3. After the inoculation, centrifuge the 96-pore cell culture plate with a centrifugal machine of Beckman-Coulter Company, centrifugal force×1500 g, centrifugal temperature 35° C. and centrifugal time 60 min.
4. After the centrifugation, suck the inoculated chlamydia trachomatis or chlamydia pneumoniae, and add 4 antibiotic drugs of serial dilution into it respectively, namely the levocarrimycin made in example 4 of the present invention; the acetylspiramycin, erythrocin and azithromycin for control, 0.1 ml/pore.

5. Culture on *chlamydia trachomatis* drug sensitive test plate at 37° C. and 5% $CO_2$ for 48 h and on *chlamydia pneumoniae* drug sensitive test plate for 72 h. After the culturing, suck antibiotic drug solution and wash it twice with PBS (0.01M, pH 7.4), and then put it in 100% methanol at room temperature for 15 min.

6. Indirect immunofluorescent staining identification: add purified *chlamydia trachomatis* resistant monoclonal antibody (N54 clone) and *chlamydia pneumoniae* resistant monoclonal antibody (P33 clone), in *chlamydia trachomatis* and *chlamydia pneumoniae* drug sensitive test plate respectively, and incubate in 50 μl/pore and 37° C. wet box for 30 min. Wash the plate with a plate washer for 4 times, and then add in rabbit anti-rat fluorescent antibody (Sigma Company), 50 μl/pore. Incubate and wash the plate by using the same method and at the same conditions. Add in mounting glycerol, 100 μl/pore, and observe the results under Nikon inverted fluorescence microscope (Diaphot-200).

7. Definition of MIC: It refers to the minimal antibiotic diluted concentration on that makes the growth of *Chlamdia Trachomatis* or *Chlamdia Pneumoniae* incursion bodies in 96-pore test plates completely suppressed (No fluorescence staining incursion is found in pores).

Test results are as follows:

TABLE 6

Minimal inhibitory concentration (MIC) in vitro inhibition of four macrolide antibiotics against *chlamydia trachomatis* and *chlamydia pneumoniae*

|  | Carrimycin μg/ml | Acetyl spiramycin (AT-SPM) μg/ml | Erythrocin (EM) μg/ml | Azithromycin (AM) μg/ml |
|---|---|---|---|---|
| *Chlamydia trachomatis* B/TW-5/OT | 0.25 | 4 | 0.5 | 0.5 |
| *Chlamydia trachomatis* D/UW-3/Cx | 0.25 | 2 | 0.5 | 0.25 |
| *Chlamydia pneumoniae* CWL-029 | 0.016 | 0.5 | ≤0.016 | 0.032 |

1. For *chlamydia trachomatis* serotype B/TW-5/OT, the MIC of carrimycin is 0.25 μg/ml, erythrocin and azithromycin (0.5 μg/ml) comes second, and acetyl spiramycin (MIC is 4 μg/ml) comes last.
2. For *chlamydia trachomatis* serotype D/UW-3/Cx, the in vitro effect of carrimycin and azithromycin is the same, MIC is 0.25 μg/ml, being sensitive; erythrocin (0.5 μg/ml) comes second and acetyl spiramycin (MIC is 2 μg/ml) comes last.
3. For *chlamydia pneumoniae* CWL-029, the in vitro effect of carrimycin and erythrocin is the most sensitive, MIC≤0.016 μg/ml, azithromycin (MIC is 0.032 μg/ml) is more sensitive; acetyl spiramycin (MIC is 0.5 μg/ml) is poor.
4. In general, the effect of the levocarrimycin of the present invention against *Chlamydia* is better than other experimental drugs.

The same test is also conducted on the levocarrimycin or levocarrimycin preparations prepared in other examples of the present invention, and the results are similar.

Test Example 4

In Vitro Anti-Urea Plasma Urealyticum and *Chlamydia pneumoniae*

1. Test method: add U-PPLO 0.8 ml in sterile 12-pore cell culture plate (add 0.9 ml in bacteria liquid control pore and 1.0 ml in culture medium control pores).
2. Add $10^4$ CCU/ml Uu bacteria liquid 0.1 ml in every experimental pores and the final amount of bacteria in the pores is $10^3$ CCU/ml (do not add bacteria liquid in the control pore of culture medium).
3. Divide into 3 groups (100 μg/ml, 10 μg/ml and 1 μg/ml antibiotic stocksolution), Add experimental antibiotics (levocarrimycin in example 6 of the present invention, acetyl spiramycin, erythrocin and azithromycin) in each experimental pores with sterile Tip according to double degradation concentration gradient: 100 μl, 50 μl, 25 μl and 12.5 μl. (Do not add antibiotics in bacteria liquid control pore and culture medium control pore. Meanwhile, the antibiotic control pore is arranged.)
4. Blend the above pores evenly, seal the culture plate with an adhesive tape and then culture in 37° C. incubator.
5. Abserve and record the growth of Uu on 17-24 h after the test. When Uu bacteria liquid control pore shows positive growth, the mimum antibiotic concentration that can inhibit the growth of Uu is the MIC of the sample. The MIC after the test is the final MIC (24 h), Determine the MIC of anti-urea plasma urealyticum strains for 4 times and the results are as follows:

Carrimycin 0.025-0.125 μg/ml,
acetyl spiramycin 0.5 μg/ml,
erythrocin 5 μg/ml,
azithromycin 0.025-0.125 μg/ml.

The above results show that carrimycin has good anti-Uu function, which is similar to the function of azithromycin and better than that of acetyl spiramycin. The anti-Uu function of erythrocin in this test is the worst.

The same test is also conducted on levocarrimycin or levocarrimycin preparations prepared in other examples of the present invention and the results are similar.

The invention claimed is:

1. A levocarrimycin, wherein said levocarrimycin comprises a mixture of isovalerylspiramycin III, II and I as main components and contains isobutyrylspiramycin III and II, butyrylspiramycin III and II, propionylspiramycin III and II, as well as acetylspiramycin III and II, wherein the content of the isovalerylspiramycin III is not less than 30 wt %, the total content of isovalerylspiramycin III, II and I is not less than 60 wt %, and the content of acylspiramycin is 80-98 wt %; the specific optical rotation of said levocarrimycin is $[\alpha]=-52°\sim-57°$ in a solution of 0.02 g/ml chloroform at temperature of 25° C.
    wherein levoisovaleryispiramycin III is a crystal compound of levoisovalerylspiramycin III, levoisovaleryispiramycin II is a crystal compound of levoisovalerylspiramycin II, or levoisovaleryispiramycin I is a crystal compound of levoisovaleryispiramycin I;
    wherein, the crystal compound of levoisovaleryispiramycin III measured by an X-ray powder diffraction with Cu-Ka ray has characteristic peaks of 2θ at 8.0°, 10.0°, 11.2°, 11.7°, 16.4°, 19.1°, 19.6°, 20.0°, 21.4°, 22.9°, 23.6° and 29.4°;
    the crystal compound of levoisovalerylspiramycin II measured by the X-ray powder diffraction with Cu-Ka ray has characteristic peaks of 2θ at 10.0°, 11.6°, 16.4°, 17.3°, 19.1°, 21.2°, 22.1°, 22.7°, 26.4°, 26.9°, 27.5° and 31.5°;

the crystal compound of levoisovaleryispiramycin I measured by the X-ray powder diffraction with Cu-Ka ray has characteristic peaks of 2θ at 7.6°, 8.0°, 10.0°, 11.4°, 16.4°, 17.0°, 17.5°, 17.9°, 19.5°, 22.7°, 23.7° and 24.4°.

2. The levocarrimycin according to claim 1, wherein said levocarrimycin further comprises spiramycin III and three homologs of spiramycin, wherein the content of spiramycin III is no more than 1.0%, and the total content of the three homologs of spiramycin is 2.0~19 wt %.

3. The levocarrimycin according to claim 2, wherein the melting point of said levocarrimycin is 112~122° C.

4. A pharmaceutical composition of levocarrimycin, wherein said pharmaceutical composition of levocarrimycin contains the levocarrimycin according to claim 1 and a pharmaceutically acceptable carrier.

5. The pharmaceutical composition of levocarrimycin according to claim 4, wherein the content of said levocarrimycin is 10~90 wt % of the pharmaceutical composition.

6. A preparation for pharmaceutical application comprising the pharmaceutical composition of levocarrimycin according to claim 5, wherein the preparation is a liquid, solid, semisolid, or gas preparation, said liquid preparation comprises injection, infusion solution, solution, mixture, syrup, tincture, colloid, aromatic water, glycerite, colloid solution, mucilage, suspension, or emulsion; said solid preparation comprises power injection, lyophilized powder injection, tablet, capsule, powder, granula, pill, sublimed preparation, or pellicle; the semisolid preparation comprises ointment, plaster, suppository, extract or gel; and the gas preparation comprises aerosol or spray.

7. The pharmaceutical composition of levocarrimycin according to claim 4, wherein the content of said levocarrimycin is 10~1500 mg per unit formulation.

8. A preparation method for the levocarrimycin according to claim 1, comprising culture, fermentation and extraction process, wherein said culture and fermentation comprise:

culturing cloned fungal strains WSP-195 produced by spiramycin containing 4"-isovaleryl transferase gene on a slant culture-medium, inoculating it in a seed medium, then inoculating it in a fermentation medium after culturing, and controlling the fermentation process by a pH regulator; controlling the pH at 6.0~9.0, wherein variation curves for pH with time show three continuous phases, the first phase satisfies formula y1=k1×1+6.0, where $0.0227 \leq k1 \leq 0.1364$, $0 < x1 \leq 22$; the second phase satisfies y2=k2×2+b2, where $-0.0735 \leq k2 < 0$, $6.5 < b2 \leq 10.62$, $22 \leq x2 \leq 56$; and the third phase satisfies formula y3=k3×3+b3, where $0 < k3 \leq 0.0078$, $6.06 \leq b3 < 6.5$, $56 \leq x3 \leq 120$, wherein y1, y2 and y3 represent a first phase pH, a second phase pH, and a third phase pH, respectively; k1, k2 and k3 represent a first phase constant, a second phase constant, and a third phase constant, respectively; and x1, x2 and x3 represent a first phase time, a second phase time, and a third phase time, respectively.

9. The preparation method according to claim 8, wherein said pH regulator is at least one of glucose, citric acid, acetic acid, hydrochloric acid, ammonia, sodium hydroxide and potassium hydroxide.

10. The preparation method according to claim 8, wherein said extraction process comprises:

processing the fermentation liquor with aluminum sulfate to obtain a filtrate, adjusting pH to 8.5~9.0, extracting with butyl acetate, washing the butyl acetate extract with non-saline water and 1% $NaH_2PO_4$ respectively, then extracting with water of pH 2.0~2.5 to obtain an aqueous extract, adjusting pH to 4.5~5.5, volatilizing and eliminating residual butyl acetate to obtain a hydrous extract, filtering and adjusting pH to 8.5~9.0, obtaining precipitate, washing the precipitate with purified water and drying it to obtain levocarrimycin.

11. The preparation method according to claim 8, wherein said slant culture-medium contains 2% soybean cake meal, 1% glucose, 3% starch, 0.5% $CaCO_3$, 0.4% NaCl and 2% agar.

12. The preparation method according to claim 8, wherein said seed medium contains 1.5% soybean cake meal, 3.0% starch, 0.4% NaCl, 0.5% $CaCO_3$, 0.3% peptone and 0.05% $KH_2PO_4$.

13. The preparation method according to claim 8, wherein said fermentation medium contains 0.5% glucose, 6.0% starch, 0.5% yeast powder, 2.0% fish meal, 0.6% $NH_4NO_3$, 1.0% NaCl, 0.5% $CaCO_3$, 0.05% $KH_2PO_4$, 0.1% $MgSO_4$, 0.5% soybean oil and 0.02% defoaming agent.

14. The preparation method according to claim 8, wherein the culture on the slant culture-medium lasts for 8~15 days at temperature of 28~38° C.; the culture on the seed medium lasts for 40~80 hours at temperature of 25~30° C.; and the fermentation on the fermentation medium lasts for 72~120 hours at temperature of 26~30° C.

15. The preparation method according to claim 8, wherein said preparation method further comprises the following steps:

a) separating and purifying the levocarrimycin to obtain levoisovalerylspiramycin I, II or III;

b) recrystallizing the levoisovalerylspiramycin I, II or III to obtain a crystal compound of levoisovalerylspiramycin I, II or III;

c) eliminating acetonitrile in the residual levocarrimycin after separating and purifying levoisovalerylspiramycin I, II or III in step a) through rotary evaporation, then extracting with an equal amount of ethyl acetate, and eliminating the ethyl acetate in the extract through rotary evaporation to obtain a paste sample; re-dissolving the obtained sample with petroleum ether, and eliminating the petroleum ether through rotary evaporation to obtain the levocarrimycin;

d) mixing the crystal compound of levoisovalerylspiramycin I, II or III obtained in step b) with the levocarrimycin obtained in step c) to obtain the levocarrimycin, in which, the isovalerylspiramycin I, II or III is the crystal compound of levoisovalerylspiramycin I, II or III.

16. The preparation method according to claim 15, wherein said separation and purification in step a) comprises: purifying the levocarrimycin obtained in the preliminary separation with a preparative high performance liquid chromatography, preparing a chromatographic column with octadecylsilyl groups chemically bonded to a silica gel carrier (ODS), using acetonitrile and ammonium acetate buffer solution as a mobile phase in a gradient elute; recording the separated UV spectrogram through UV detection, and collecting target peaks of levoisovalerylspiramycin I, II or III components:

chromatographic column: ODS preparative chromatographic column;

mobile phase: acetonitrile (A), 100 mM ammonium acetate solution (B);

gradient condition: adopting linear gradient for 0~60 min, A is 25%~65%; and 61~90 min, A is 65%~90%;
flow velocity: 260 mL/min;
injection volume: 10 mL;
sampling concentration: 0.5 g/mL;
measurement wavelength: 231 nm;
way of collecting: collection via UV triggering;
collecting the sample of levoisovalerylspiramycin I according to retention time 44.759 min for levoisovalerylspiramycin I; or collecting the sample of isovalerylspiramycin II according to retention time 43.34 min for isovalerylspiramycin II; or collecting the sample of levoisovalerylspiramycin III according to retention time 48.009 min for levoisovalerylspiramycin III;
   then eliminating the acetonitrile through rotary evaporation, extracting with an equal amount of ethyl acetate, and eliminating the ethyl acetate in the extract through rotary evaporation to obtain a paste sample; re-dissolving the obtained sample with petroleum ether, and eliminating the petroleum ether through rotary evaporation to obtain a white solid powder of levoisovalerylspiramycin I, II or III.

17. The preparation method according to claim 16, wherein when the isovalerylspiramycin I is a crystal of levoisovalerylspiramycin I, the crystal is obtained through the following recrystallization process: dissolving the white solid powder of levoisovalerylspiramycin I in a mixed solvent of absolute methanol, absolute ethyl alcohol and anhydrous acetone, then adding pure water while stirring, after that, reducing the temperature to 5° C.~15° C. while stirring continuously, to obtain the crystal of levoisovalerylspiramycin I, in which the volume ratio of ethyl acetate to absolute ethyl alcohol to anhydrous acetone in the mixed solvent is 1:0.1~10:0.5~1;
when the isovalerylspiramycin II is a crystal of levoisovalerylspiramycin II, the crystal is obtained through the following recrystallization process: dissolving the white solid powder of levoisovalerylspiramycin II in a mixed solvent of absolute methanol, absolute ethyl alcohol and anhydrous acetone, then adding pure water while stirring, after that, reducing the temperature to 5° C.~15° C. while stirring continuously, to obtain the crystal of the levoisovalerylspiramycin II, in which the volume ratio of absolute methanol to absolute ethyl alcohol to anhydrous acetone in the mixed solvent is 1:0.1~10:0.5~1;
when the isovalerylspiramycin III is a crystal of levoisovalerylspiramycin III, the crystal is obtained through the following recrystallization process: dissolving the white solid powder of levoisovalerylspiramycin III in a mixed solvent of absolute methanol, absolute ethyl alcohol and anhydrous acetone, then adding pure water while stirring, after that, reducing the temperature to 5° C.~15° C. while stirring continuously, to obtain the crystal of the levoisovalerylspiramycin III, in which the volume ratio of absolute methanol to absolute ethyl alcohol to anhydrous acetone in the mixed solvent is 1:0.1~10:0.5~1.

18. The levocarrimycin according to claim 1, wherein the content of acylspiramycin is 90~98%.

19. The levocarrimycin according to claim 1, wherein the content of acylspiramycin is 95~98%.

20. The levocarrimycin according to claim 2, wherein the total content of the three homologs of spiramycin is 2.0~9.0 wt %.

21. The levocarrimycin according to claim 2, wherein the total content of the three homologs of spiramycin is 2.0~4.0 wt %.

22. The pharmaceutical composition of levocarrimycin according to claim 5, wherein the content of said levocarrimycin is 25~75 wt % of the pharmaceutical composition.

23. The pharmaceutical composition of levocarrimycin according to claim 5, wherein the content of said levocarrimycin is 40~60 wt % of the pharmaceutical composition.

24. The pharmaceutical composition of levocarrimycin according to claim 7, wherein the content of said levocarrimycin is 200~500 mg per unit formulation.

* * * * *